(12) United States Patent
Shiratsuchi et al.

(10) Patent No.: US 10,041,892 B2
(45) Date of Patent: Aug. 7, 2018

(54) CHARGED PARTICLE BEAM INSPECTION APPARATUS AND CHARGED PARTICLE BEAM INSPECTION METHOD

(71) Applicant: NuFlare Technology, Inc., Yokohama-shi (JP)

(72) Inventors: Masataka Shiratsuchi, Kawasaki (JP); Chosaku Noda, Yokohama (JP); Riki Ogawa, Kawasaki (JP)

(73) Assignee: NuFlare Technology, Inc., Yokohama-shi (JP)

( * ) Notice: Subject to any disclaimer, the term of this patent is extended or adjusted under 35 U.S.C. 154(b) by 0 days.

(21) Appl. No.: 15/652,994

(22) Filed: Jul. 18, 2017

(65) Prior Publication Data

US 2018/0031498 A1    Feb. 1, 2018

(30) Foreign Application Priority Data

Jul. 27, 2016  (JP) ................. 2016-146962

(51) Int. Cl.
*G01N 23/22*      (2018.01)
*G01N 23/2251*   (2018.01)
(Continued)

(52) U.S. Cl.
CPC ...... *G01N 23/2251* (2013.01); *H01J 37/1474* (2013.01); *H01J 37/20* (2013.01); *H01J 37/22* (2013.01); *G01N 2223/3301* (2013.01); *G01N 2223/3307* (2013.01); *G01N 2223/426* (2013.01); *G01N 2223/6116* (2013.01)

(58) Field of Classification Search
CPC ....... G01N 23/2251; G01N 2223/3301; G01N 2223/3307; G01N 2223/426; G01N 2223/6116; H01J 37/1474; H01J 37/20; H01J 37/22; H01J 37/28; H01J 37/045
See application file for complete search history.

(56) References Cited

U.S. PATENT DOCUMENTS 8,362,425 B2 * 1/2013 Han .................. G01N 23/2251
                                                        250/306
2005/0214958 A1 * 9/2005 Nakasuji ............. G01N 23/225
                                                          438/14
(Continued)

FOREIGN PATENT DOCUMENTS

JP    2003-188221    7/2003
JP    2011-185845    9/2011
(Continued)

*Primary Examiner* — David E Smith
(74) *Attorney, Agent, or Firm* — Oblon, McClelland, Maier & Neustadt, L.L.P.

(57) ABSTRACT

A charged particle beam inspection apparatus includes a first deflector to deflect N×N' multiple beams collectively to N×N' small regions having a size p/M in the first direction and arrayed at the pitch p in the first direction, perform tracking deflection, and re-deflect the multiple beams collectively to next N×N' small regions away from the N×N' small regions by N small regions in the first direction, by the stage completes a movement of a distance of N/M×p so as to reset the tracking deflection; and a second deflector to deflect the multiple beams collectively to scan the N×N' small regions concerned while the tracking deflection is performed.

10 Claims, 14 Drawing Sheets

(51) Int. Cl.
*H01J 37/147* (2006.01)
*H01J 37/20* (2006.01)
*H01J 37/22* (2006.01)

(56) References Cited

U.S. PATENT DOCUMENTS

| 2010/0320382 | A1* | 12/2010 | Almogy | H01J 37/05 |
| | | | | 250/307 |
| 2012/0061565 | A1* | 3/2012 | Enyama | H01J 37/265 |
| | | | | 250/307 |
| 2013/0056645 | A1* | 3/2013 | Yoshikawa | H01J 37/305 |
| | | | | 250/396 R |

FOREIGN PATENT DOCUMENTS

| JP | 2011-232646 | 11/2011 |
| JP | 5429025 | 2/2014 |
| JP | 5763298 | 8/2015 |

\* cited by examiner

FIG.12

# CHARGED PARTICLE BEAM INSPECTION APPARATUS AND CHARGED PARTICLE BEAM INSPECTION METHOD

CROSS-REFERENCE TO RELATED APPLICATION

This application is based upon and claims the benefit of priority from prior Japanese Patent Application No. 2016-146962 filed on Jul. 27, 2016 in Japan, the entire contents of which are incorporated herein by reference.

BACKGROUND OF THE INVENTION

Field of the Invention

Embodiments described herein relate generally to a charged particle beam inspection apparatus and a charged particle beam inspection method. The present invention relates, for example, to an inspection apparatus that inspects a pattern by acquiring a secondary electron image of a pattern emitted through irradiation with multiple electron beams.

Related Art

In recent years, the circuit line width required for a semiconductor element has been getting narrower with the increase in integration and capacity of a large scale integrated circuit (LSI). A semiconductor element of this type may be manufactured by forming a circuit through exposure-transferring a pattern on a wafer by a reduction stepper, which may be called a stepper, by using an original pattern (mask or reticle, hereinafter referred to as mask) on which a circuit pattern is formed.

For manufacturing LSIs requiring a large manufacturing cost, improvement of yield is essential. However, as represented by 1 gigabit class DRAM (Random Access Memory), patterns constituting LSIs are on the order of submicrons to nanometers. In recent years, with miniaturization of LSI patterns formed on semiconductor wafers, the size of a pattern defect required to be detected is becoming extremely small. Therefore, there is a need for higher accuracy of a pattern inspection apparatus that inspects defects of ultrafine patterns transferred onto a semiconductor wafer. Besides, as one of the major factors of lowering the yield, pattern defects of masks used when ultrafine patterns are exposed and transferred onto a semiconductor wafer by photolithography technology can be mentioned. Therefore, there is a need for higher accuracy of a pattern inspection apparatus that inspects defects of transfer masks used for LSI manufacture.

As an inspection method, a method for inspecting by comparing an optical image acquired by imaging a pattern formed on a substrate such as a semiconductor wafer or a lithography mask at a predetermined magnification using a magnifying optics with a design data or an optical image acquired by imaging the same pattern on a target object is known. For example, as a pattern inspection method, there are "die to die inspection" and "die to database inspection". In "die to die inspection", optical image data items acquired by imaging the same pattern at different positions on the same mask are compared. In "die to database inspection", pattern data (design pattern data) that has been converted into a device input format to be input by the pattern generating (or "writing") apparatus at the time of generating a pattern with CAD data of pattern design as a mask is input to the inspection apparatus, design image data (reference image) is generated based on the pattern data, and the design image data and an optical image as measurement data after imaging the pattern are compared. In the inspection methods in such an inspection apparatus, a substrate to be inspected is placed on a stage, and light flux scans the target object through the movement of the stage, whereby inspection is performed. The substrate to be inspected is irradiated with a light flux by a light source and an illumination optics. Light that has been transmitted or reflected through/by the substrate to be inspected is imaged on the sensor via the optics. The image captured by the sensor is transmitted as measurement data to a comparator circuit. The comparator circuit compares, after alignment of the images with each other, the measurement data and reference data according to an appropriate algorithm, and determines that there is a pattern defect when they do not match.

In the above-described pattern inspection apparatus, an optical image is acquired by irradiating a substrate to be inspected with a laser beam and capturing a transmission image or a reflected image of the laser beam. On the other hand, the development for an inspection apparatus that acquires a pattern image by irradiating a substrate to be inspected with multiple beams composed of a plurality of electron beams in an array arrangement in which a plurality of rows of beams are arrayed at an equal pitch on a straight line, and detecting secondary electrons corresponding to the respective beams emitted from the substrate to be inspected. In a pattern inspection apparatus using an electron beam including such multiple beams, secondary electrons are detected by scanning each of small regions of the substrate to be inspected. In doing so, a step-and-repeat operation is carried out, in which the position of the substrate to be inspected is fixed while the beam is being scanned, and the position of the substrate to be inspected is moved to a next small region when the scan is completed. Since multiple beams can be arranged within a limited region by using a multiple beams in an array arrangement in which a plurality of rows of beams are arranged at an equal pitch on a straight line are used, simultaneous scanning of many small regions is possible. Therefore, improvement of throughput is expected. However, in the step-and-repeat operation, the settling time (overhead time) until the stage position is stabilized is required every time when the stage moves. Since one scanning range (small region) is small, in order to scan the entire substrate, the number of steps to move the stage is enormous. Therefore, unnecessary time not required for scanning is caused for a time length obtained by multiplying the settling time to the number of steps. There is also an estimate that a period of time not required for scanning of, for example, 80 hours or more is caused for one substrate even when scanning over the substrate is performed using multiple beams.

Therefore, in order to improve the throughput of the inspection apparatus, it is studied to change the method of moving the stage from the step-and-repeat operation method to the continuous movement method, which does not require settling time for each step. However, when scanning is performed with multiple beams arranged in an array arrangement, the settling time can be made unnecessary in the continuous movement method, but instead small regions are transferred into scanning ranges of a plurality of beams arranged in the moving direction sequentially. As a result, unnecessary scanning is repeated for the small regions, the pattern images of which have been already acquired Therefore, the method does not lead to an improvement in throughput as well. In order not to repeat such unnecessary scanning, it is necessary to increase the deflection width for deflecting the multiple beams so as to skip regions that have been already scanned and scan the next small region. However, if the deflection width of the beam deflection is increased, the influence of the aberration of the electron optics becomes large, making it difficult to sufficiently narrow each beam, causing so-called blurring.

An inspection apparatus that scans a target object while continuously moving the stage in the y direction using multiple beams in which the beams are arranged along the circumference so as to be equally spaced in the x direction is being studied (For example, JP 2003-188221 A). However, such a technique is difficult to apply to multiple beams arranged in a matrix of rows and columns.

BRIEF SUMMARY OF THE INVENTION

According to one aspect of the present invention, a charged particle beam inspection apparatus includes a movable stage on which an inspection target substrate is placed; a stage control circuit configured to continuously move the stage in a direction opposite to a first direction; a first deflector configured to deflect multiple beams composed of a plurality of charged particle beams arrayed in N (N is an integer of 2 or larger) rows at an equal pitch p in the first direction and N' (N' is an integer of 1 or larger) columns in a second direction that is orthogonal to the first direction on the substrate collectively to a group of N×N' small regions arrayed in N rows at the pitch p in the first direction and N' columns in the second direction among a plurality of small regions obtained by dividing an inspection region of the substrate by a size p/M (M is an integer of 2 or larger) in the first direction and a predetermined size in the second direction, perform tracking deflection of the multiple beams such that the multiple beams follow movement of the stage while the stage continuously moves a distance obtained by N/M×p in the direction opposite to the first direction, and re-deflect the multiple beams collectively to a next group of N×N' small regions arrayed at the pitch p in the first direction, the next group being away from the group of N×N' small regions by N small regions in the first direction by the stage completes the movement of the distance obtained by N/M×p in the opposite direction of the first direction so as to reset the tracking deflection; a second deflector configured to deflect the multiple beams collectively such that the group of N×N' small regions concerned are scanned while the tracking deflection of the multiple beams are performed to follow the continuous movement of the stage; and a detector configured to detect secondary electrons emitted from the substrate due to irradiating the substrate with the multiple beams, wherein a combination of the numbers N and M that has one as the greatest common divisor is used.

According to another aspect of the present invention, a charged particle beam inspection method includes deflecting multiple beams composed of a plurality of charged particle beams arrayed in N (N is an integer of 2 or larger) rows at an equal pitch p in a first direction and N' (N' is an integer of 1 or larger) columns in a second direction that is orthogonal to the first direction on an inspection target substrate collectively to a group of N×N' small regions arrayed in N rows at the pitch p in the first direction and N' columns in the second direction among a plurality of small regions obtained by dividing an inspection region of the substrate by a size p/M (M is an integer of 2 or larger) in the first direction and a predetermined size in the second direction, and scanning the N×N' small regions while performing tracking deflection of the multiple beams such that the multiple beams follow movement of a stage on which the inspection target substrate is placed while the stage continuously moves a distance obtained by N/M×p in a direction opposite to the first direction; detecting secondary electrons emitted from the substrate due to irradiating the substrate with the multiple beams; and performing tracking reset by re-deflecting the multiple beams collectively to a next group of N×N' small regions arrayed at the pitch p in the first direction, the next group being away from the group of N×N' small regions by N small regions by the stage completes the movement of the distance obtained by N/M×p in the opposite direction of the first direction, wherein the scanning, the detecting, and the performing tracking reset are repeated while the stage continuously moves in the direction opposite to the first direction using a combination of the numbers N and M that has one as the greatest common divisor.

BRIEF DESCRIPTION OF THE DRAWINGS

FIG. 12 is a conceptual diagram for describing an example of the relationship between sub regions and corresponding beams in the scanning operation according to the first embodiment;

DETAILED DESCRIPTION OF THE INVENTION

Hereinafter, in the embodiment, an inspection apparatus and a method capable of reducing a deflection width of beam deflection in a pattern inspection in which a stage is continuously moved using multiple beams including a plurality of beams arranged in the moving direction of the stage is described.

In the following embodiment, a case where an electron beam is used as an example of the charged particle beam will be described. However, a charged beam is not limited to an electron beam. Other charged particle beams such as an ion beam may be used.

First Embodiment

Figure 1:
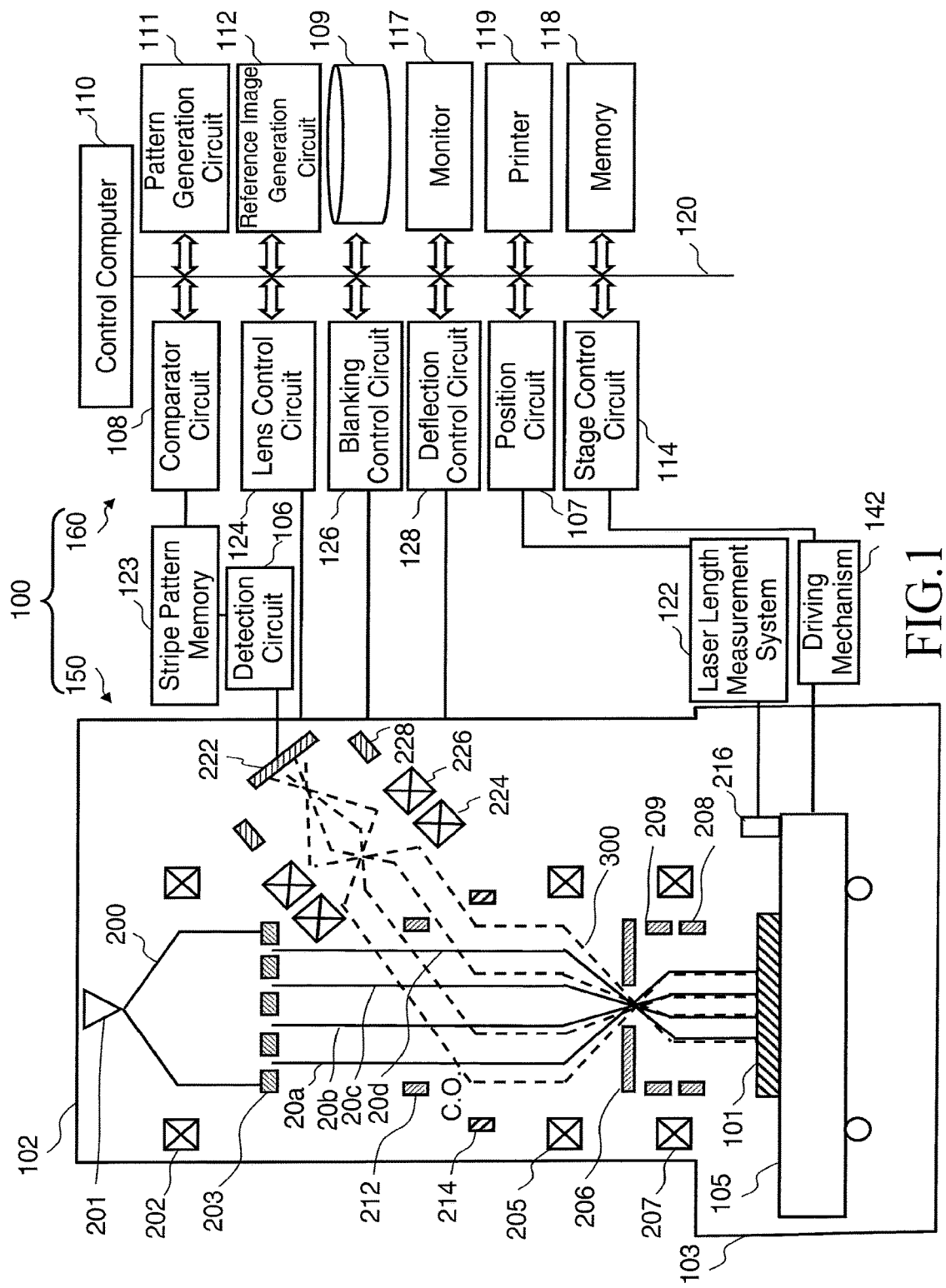
FIG. 1 is a configuration diagram illustrating a configuration of a pattern inspection apparatus according to a first embodiment.

FIG. 1 is a configuration diagram illustrating a configuration of a pattern inspection apparatus according to a first embodiment. In FIG. 1, an inspection apparatus 100 that inspects a pattern formed on a substrate is an example of a charged particle beam inspection apparatus. The inspection apparatus 100 includes an electro-optical image acquisition mechanism 150 and a control system circuit 160 (control unit). The electro-optical image acquisition mechanism 150 includes an electron beam column 102 (electron optical column), an inspection chamber 103, a detection circuit 106, a stripe pattern memory 123, a stage driving mechanism 142, and a laser length measurement system 122. Inside the electron beam column 102, an electron gun assembly 201, an illumination lens 202, a shaping aperture array substrate 203, a reduction lens 205, a limiting aperture substrate 206, an objective lens 207, a main deflector 208, a sub deflector 209, a collective blanking deflector 212, a beam separator 214, projection lenses 224 and 226, a deflector 228, and a multi-detector 222 are arranged.

In the inspection chamber 103, an XY stage 105 movable at least on an XY plane is disposed. On the XY stage 105, a substrate 101 on which a chip pattern to be inspected is formed is disposed. The substrate 101 includes a semiconductor substrate such as an exposure mask or a silicon wafer. The substrate 101 is disposed on the XY stage 105 with, for example, its pattern formation surface facing upward. Further, on the XY stage 105, a mirror 216 that reflects a laser beam for measuring laser length emitted from the laser length measurement system 122 disposed outside the inspection chamber 103 is disposed. The multi-detector 222 is connected to the detection circuit 106 outside the electron beam column 102. The detection circuit 106 is connected to the stripe pattern memory 123.

In the control circuit 160, a control computer 110, which is a computer, is connected to a position circuit 107, a comparator circuit 108, a pattern generation circuit 111, a reference image generation circuit 112, a stage control circuit 114, a lens control circuit 124, a blanking control circuit 126, a deflection control circuit 128, a storage device 109 such as a magnetic disk drive, a monitor 117, a memory 118, and a printer 119 through a bus 120. The stripe pattern memory 123 is connected to the comparator circuit 108. The XY stage 105 is driven by the driving mechanism 142 under the control of the stage control circuit 114. In the driving mechanism 142, for example, a driving system such as a three-axis (X-Y-θ) motor that drives in the X direction, the Y direction, and the θ direction is configured to allow movement of the XY stage 105. As the X motor, Y motor, and θ motor (not illustrated), for example, step motors can be used. The XY stage 105 is movable in the horizontal directions and the rotation direction by respective motors of X, Y and θ axes. The moving position of the XY stage 105 is measured by the laser length measurement system 122 and supplied to the position circuit 107. The laser length measurement system 122 measures the position of the XY stage 105 according to the principle of the laser interferometry by receiving light having been reflected from the mirror 216.

A high voltage power supply circuit (not illustrated) is connected to the electron gun assembly 201, and acceleration voltage is applied between a filament and an extraction electrode (not illustrated) in the electron gun assembly 201 from a high voltage power supply circuit. In addition, predetermined voltage is applied to the extraction electrode, and a cathode (filament) is heated to a predetermined temperature. Due to such application of voltage and heating, the electrons emitted from the cathode are accelerated and are released as an electron beam. For example, electromagnetic lenses are used as the illumination lens 202, the reduction lens 205, the objective lens 207, and the projection lenses 224 and 226, and all of them are controlled by the lens control circuit 124. The beam separator 214 is also controlled by the lens control circuit 124. The collective blanking deflector 212 and the deflector 228 are each constituted by an electrode group of at least two poles, and are controlled by the blanking control circuit 126. The main deflector 208 and the sub deflector 209 are each constituted by an electrode group of at least four electrodes, and are controlled by the deflection control circuit 128.

When the substrate 101 is a semiconductor wafer with a plurality of chip (die) patterns formed thereon, pattern data of the chip (die) patterns is input from the outside of the inspection apparatus 100 and stored in the storage device 109. When the substrate 101 is an exposure mask, design pattern data that is a basis for forming a mask pattern on the exposure mask is input from the outside of the inspection apparatus 100 and stored in the storage device 109.

Here, in FIG. 1, components needed to describe a first embodiment are illustrated. The inspection apparatus 100 may include other components that are generally required.

Figure 2:
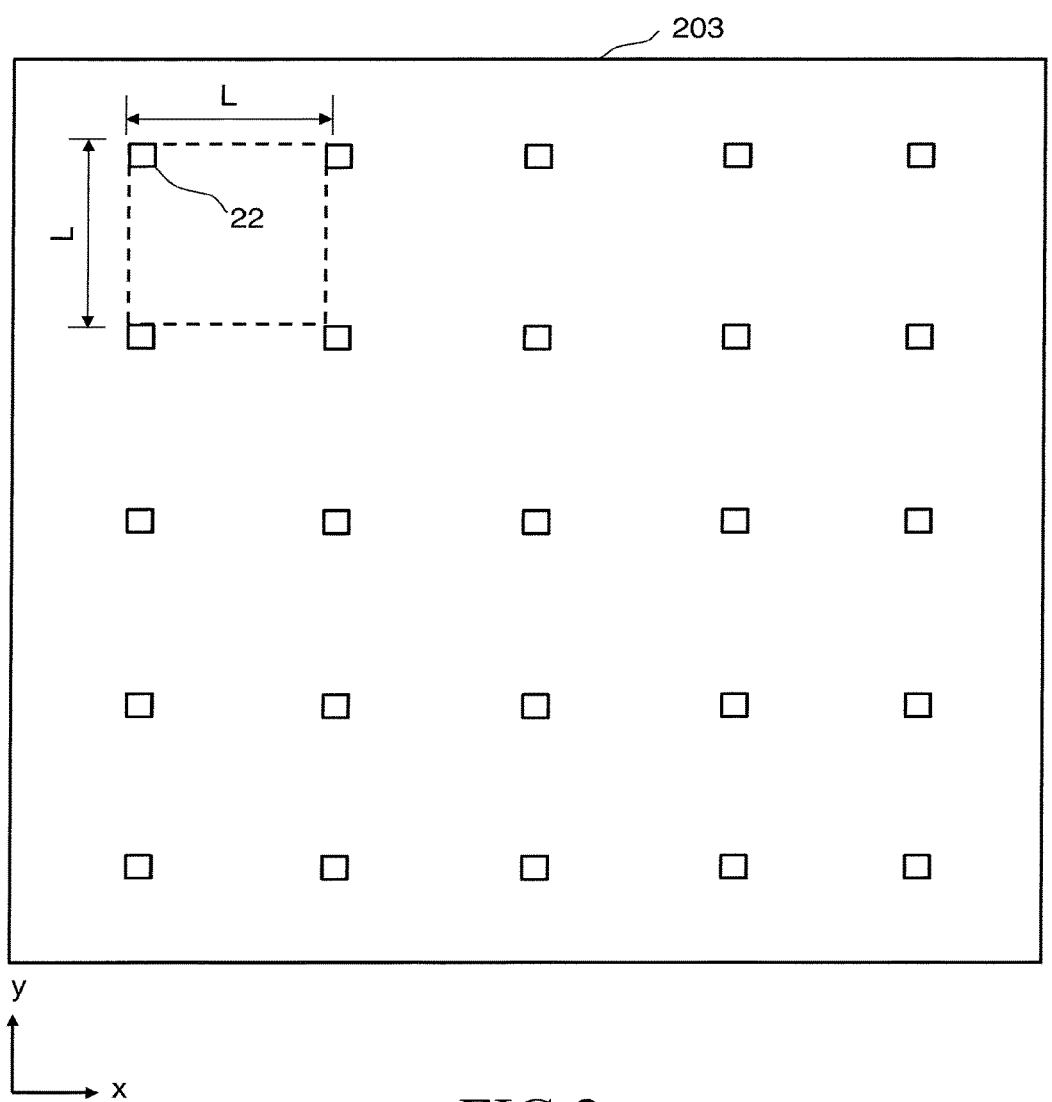
FIG. 2 is a conceptual diagram illustrating a configuration of a shaping aperture array substrate according to the first embodiment.

FIG. 2 is a conceptual diagram illustrating a configuration of the shaping aperture array substrate according to the first embodiment. In FIG. 2, the shaping aperture array substrate 203 is formed with holes (openings) 22 in two dimensions (matrix of rows and columns) of N rows in crosswise (x direction)×N' columns in lengthwise (y direction) (N is an integer of 2 or larger, and N' an integer of 1 or larger) at a predetermined arrangement pitch L in the x and y directions (x: first direction and y: second direction). When the reduction magnification of the multiple beams is "a" (when the substrate 101 is irradiated with the multiple beams having a diameter reduced to 1/a), and the pitch between beams of the multiple beams in the x and y directions on the substrate 101 is p, the arrangement pitch is L=(a×p). The example of FIG. 2 illustrates a case where holes 22 for forming multiple beams of 5×5 where N=5 and N'=5 are formed. Next, the operation of the electro-optical image acquisition mechanism 150 in the inspection apparatus 100 will be described.

Figure 3:
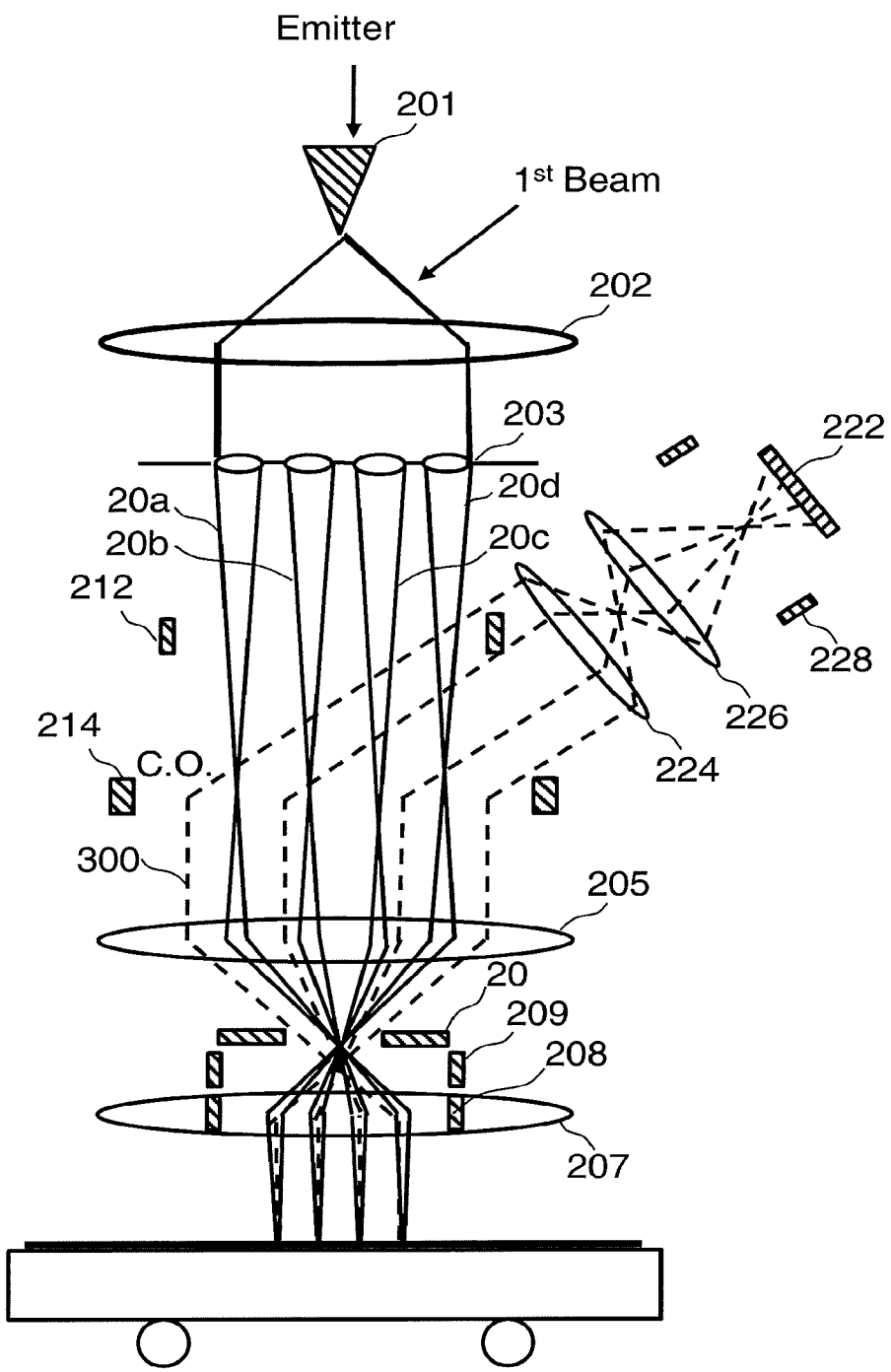
FIG. 3 is a diagram for describing a beam trajectory in the inspection apparatus according to the first embodiment.

FIG. 3 is a diagram for describing a beam trajectory in the inspection apparatus according to the first embodiment. An electron beam 200 emitted from the electron gun assembly 201 (emission source) illuminates whole of the shaping aperture array substrate 203 almost vertically by the illumination lens 202. As illustrated in FIG. 2, a plurality of rectangular holes 22 (openings) are formed in the shaping aperture array substrate 203, and the electron beam 200 illuminates a region covering all of the plurality of holes 22. Respective parts of the electron beams 200 with which the positions of the plurality of holes 22 are irradiated pass through the plurality of holes 22 of the shaping aperture array substrate 203 respectively, whereby a plurality of electron beams, for example, having rectangular or circular shape (multiple beams) (the plurality of electron beams) 20a to 20d (solid lines in FIGS. 1 and 3) are formed.

The formed multiple beams 20a to 20d subsequently form crossovers (C.O.), pass through the beam separator 214 disposed at the crossover position of the multiple beams 20, are then reduced by the reduction lens 205, and travels toward the center hole formed in the limiting aperture substrate 206. Here, when all of the multiple beams 20a to 20d are collectively deflected by the collective blanking deflector 212 disposed between the shaping aperture array substrate 203 and the reduction lens 205, the multiple beams 20a to 20d are off the center hole of the limiting aperture substrate 206 and are shielded by the limiting aperture substrate 206. On the other hand, the multiple beams 20a to 20d that have not been deflected by the collective blanking deflector 212 pass through the center hole of the limiting aperture substrate 206 as illustrated in FIG. 1. Blanking control is performed by turning ON/OFF the collective blanking deflector 212, and ON/OFF of the beams is collectively controlled. In this manner, the limiting aperture substrate 206 shields the multiple beams 20a to 20d that have been deflected by the blanking deflector 212 to make the beam OFF state. The multiple beams 20a to 20d are then formed from the group of beams having passed through the limiting aperture substrate 206 that are formed from the time when the beams are ON to the time when the beams are OFF. The multiple beams 20a to 20d that have passed through the limiting aperture substrate 206 are focused by the objective lens 207 and make a pattern image (beam diameter) of a desired reduction ratio, and the main deflector 208 and the sub deflector 209 deflect all of the multiple beams 20 that have passed through the limiting aperture substrate 206 collectively in the same direction. Thus with the respective multiple beams, their respective irradiation positions on the substrate 101 are irradiated. In such a case, the main deflector 208 collectively deflects all of the multiple beams 20 such that a reference position of a unit inspection region to be scanned by each beam, which is to be described later, is irradiated with each of the beams, and also, performs tracking deflection such that the multiple beams 20 follow the movement of the XY stage 105. The sub deflector 209 then collectively deflects all of the multiple beams 20 such that each of the beams scans N×N' sub regions (grids 29 to be described later) in the corresponding unit inspection region. Ideally, the multiple beams 20 with which irradiation is performed at a time are arranged at a pitch obtained by multiplying the arrangement pitch L (=ap) of the plurality of holes 22 of the shaping aperture array substrate 203 by the above-described desired reduction ratio (1/a). In this manner, the electron beam column 102 irradiates the substrate 101 with N×N' multiple beams 20 two-dimensionally at a time. Due to the irradiation with the multiple beams 20 at desired positions on the substrate 101 (dotted lines in FIGS. 1 and 3), a flux of secondary electrons (multiple secondary electrons 300) corresponding to respective beams of the multiple beams 20 is emitted from the substrate 101.

The multiple secondary electrons 300 emitted from the substrate 101 are refracted toward the center of the multiple secondary electrons 300 by the objective lens 207 and proceed toward the center hole formed in the limiting aperture substrate 206. The multiple secondary electrons 300 that have passed through the limiting aperture substrate 206 are refracted substantially parallel to the optical axis by the reduction lens 205 and travel to the beam separator 214.

Here, the beam separator 214 generates an electric field and a magnetic field in a direction orthogonal to each other on a plane orthogonal to the traveling direction (optical axis) of the multiple beams 20. The electric field exerts force in an identical direction regardless of the traveling direction of electrons. In contrast, the magnetic field exerts force according to Fleming's left-hand rule. Therefore, it is possible to change the direction of force acting on the electrons depending on the entering direction of the electrons. The force acting on the multiple beams 20 (primary electron beams) entering the beam separator 214 from the upper side due to the electric field and the force acting thereon due to the magnetic field cancel each other, and thus the multiple beams 20 travel straight downward. On the other hand, on the multiple secondary electrons 300 entering the beam separator 214 from the lower side, the force by the electric field and the force by the magnetic field both work in the same direction, and thus the multiple secondary electrons 300 are bent obliquely upward.

The multiple secondary electrons 300 having been bent obliquely upward are projected onto the multi-detector 222 while being refracted by the projection lenses 224 and 226. The multi-detector 222 detects the projected multiple secondary electrons 300. The multi-detector 222 has a diode type two-dimensional sensor (not illustrated). Then, at a diode-type two-dimensional sensor position corresponding to each beam of the multiple beams 20, each secondary electron of the multiple secondary electrons 300 collides with a diode-type two-dimensional sensor to generate an electron and generate secondary electron image data for each pixel to be described later. When the multi-detector 222 does not detect the multiple secondary electrons 300, the multiple secondary electrons 300 can be made not to reach the light receiving surface by blanking-deflect of the multiple secondary electrons 300 by the deflector 228.

Figure 4:
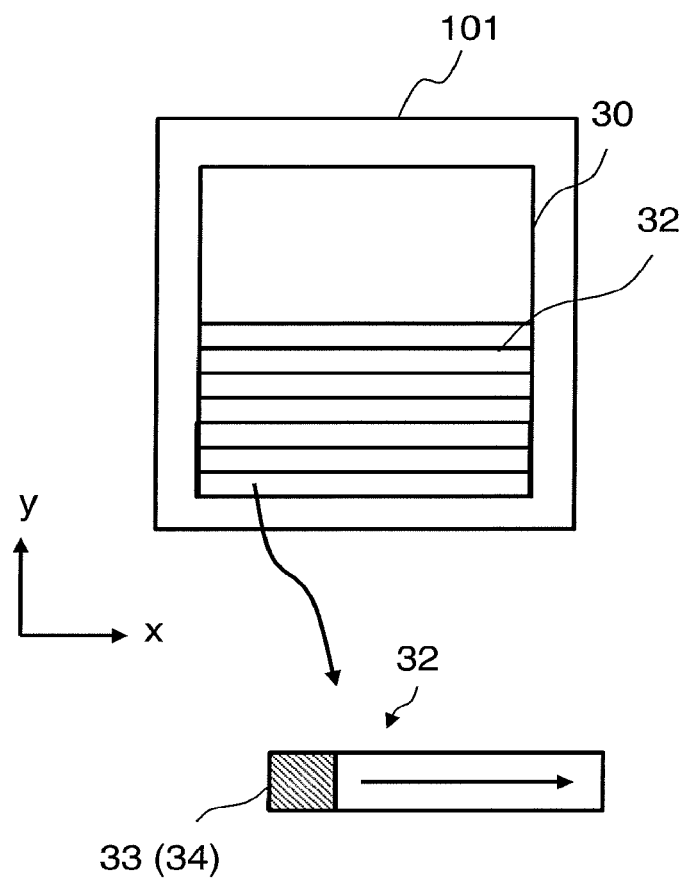
FIG. 4 is a conceptual diagram for describing an example of scanning operation according to the first embodiment.

FIG. 4 is a conceptual diagram for describing an example of scanning operation according to the first embodiment. In FIG. 4, the inspection region 30 of the substrate 101 is virtually divided into a plurality of stripe regions 32 each having a predetermined width in the y direction, for example. For example, it is preferable to use a mask substrate for exposure as the substrate 101. For example, the inspection region 30 may be virtually divided into a plurality of stripe-shaped stripe regions 32 having the same width as the natural number multiple of the width of the irradiation region 34 that can be irradiated through one irradiation with all of the multiple beams 20. In the example of FIG. 4, the inspection region 30 is virtually divided into a plurality of stripe-shaped stripe regions 32 having the same width as the width of the irradiation region 34. First, the XY stage 105 is moved to adjust a tracking region 33 such that the irradiation region 34 that can be irradiated by one irradiation with the multiple beams 20 is located at a position that is outside of a first stripe region 32 by the size of one irradiation region 34 from the left end of the first stripe region 32, for example, and a scanning operation is started. In the first embodiment, the XY stage 105 is moved continuously in the −x direction (the opposite direction to the first direction), for example, at a uniform speed, a group of sub regions arranged at the pitch p in the desired tracking region 33 is scanned while moving the irradiation region 34 so as to follow the continuous movement, and after completion of the scanning, the irradiation region 34 is moved to a next tracking region 33 in the x direction (the first direction) to reset tracking. By repeating this operation, the stripe regions 32 are sequentially scanned in the x direction. In scanning the first stripe region 32, the XY stage 105 is moved, for example, in the −x direction, so that the scanning operation is relatively advanced in the x direction. When irradiation of the first stripe region 32 with the multiple beams is completed, the stage position is moved in the −y direction to adjust the irradiation region 34 such that the irradiation region 34 is located at a position that is outside of a second stripe region 32 by the size of the one irradiation region 34 from the right end of the second stripe region 32, for example and relatively in y direction. Irradiation with the multiple beams is similarly performed in −x direction by, for example, moving the XY stage 105, for example, in the x direction this time. In the third stripe region 32, irradiation with the multiple beams is performed in the x direction, and in the fourth stripe region 32, irradiation with the multiple beams is performed in the −x direction. In such a manner the scanning is performed while changing the direction alternately, so that inspection time can be reduced. However, the present invention is not limited to the scanning in such alternating directions, but scanning may be proceeded in the same direction in forming patterns in the respective stripe regions 32. The multiple beams 20 formed by passing through the respective holes 22 of the shaping aperture array substrate 203 enable detection of multiple secondary electrons 300 formed of a flux of secondary electrons corresponding to a plurality of beams (primary electron beams) at once, the number of which is the same as the number of the holes 22 at most.

Figure 5:
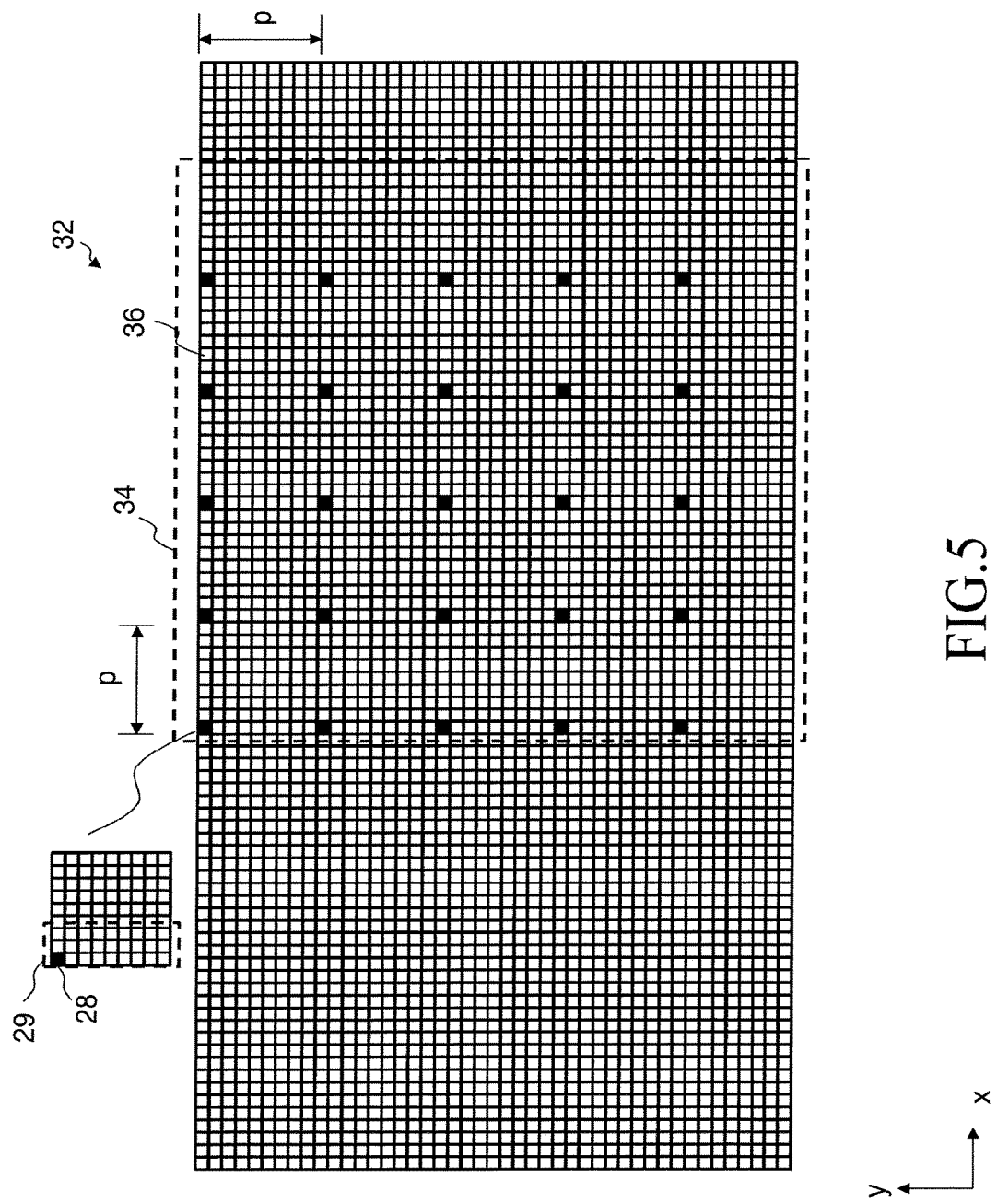
FIG. 5 is a view illustrating an example of irradiation regions of multiple beams and measurement pixels according to the first embodiment.

FIG. 5 is a view illustrating an example of irradiation regions of multiple beams and measurement pixels according to the first embodiment. In FIG. 5, each of the stripe regions 32 is divided into a plurality of mesh-like mesh regions each having a beam size of the multiple beams, for example. The respective mesh regions are measurement pixels 36 (unit irradiation regions). A plurality of measurement pixels 28 (the irradiation positions of the beams at one shot) that can be irradiated by one irradiation with N×N' multiple beams 20 is illustrated in the irradiation region 34. In other words, the pitch p between the adjacent measurement pixels 28 in the x and y directions is the pitch between the beams of the multiple beams 20 on the substrate 101. In the example of FIG. 5, one measurement pixel 28 out of four adjacent measurement pixels 28 is set as one of the four corners of a rectangle. From the measurement pixel 28 as a start point, a region surrounded by p×p in the x and y directions is divided by a division number M (M is an integer of 2 or larger) to form one grid 29 (sub region, small region) having a size of p/M in the x direction and p in the −y direction. FIG. 5 illustrates an example in which each grid 29 (individual beam scan region) includes 3×9 pixels.

Figure 6:
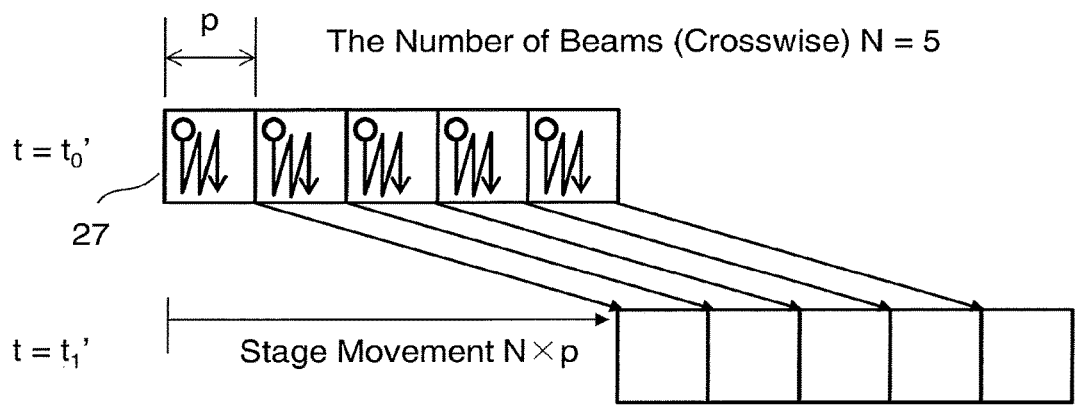
FIG. 6 is a conceptual diagram for describing an example of details of scanning operation according to a comparative example of the first embodiment.

FIG. 6 is a conceptual diagram for describing an example of details of a scanning operation according to a comparative example of the first embodiment. In the example of FIG. 6, as a comparative example of the first embodiment, N multiple beams corresponding to one column in the y direction are illustrated out of N×N' multiple beams 20. Here, N=5 multiple beams arranged in the x direction at an equal pitch p are illustrated. In the comparative example of the first embodiment, a case where each beam of N=5 multiple beams arranged in the x direction at an equal pitch p scans a whole region 27 surrounded by p×p in the x and y directions starting from the measurement pixel 28 of the beam, and then scans a next region 27 surrounded by p×p is illustrated. In the comparative example of the first embodiment, the stage speed is adjusted such that the XY stage 105 moves by N×p while each of the multiple beams scans each region surrounded by p×p (t=t0' to t1'). During the time, the main deflector 208 performs tracking deflection such that the deflecting operation of the sub deflector 209 allows each beam to scan a region surrounded by p×p. At the time (t=t1') when the scanning of N regions 27 each surrounded by p×p arranged consecutively in the x direction is completed, N=5 multiple beams are collectively deflected in the x direction such that the scan regions do not overlap with each other to reset tracking. By repeating this operation, scanning of a region on a continuously moving stage with multiple beams is possible without the scan regions overlapping with each other. In the example of FIG. 6, it is necessary to deflect the multiple beams in the x direction (or −x direction) by (N−1)×p (=4p). Therefore, in the comparative example of the first embodiment, the deflection width of the beam deflection in the x direction (or −x direction) is required to be (N−1)×p. On the other hand, the deflection width of the beam deflection in the y direction (or −y direction) is required to be p. When the number N of beams increases, the deflection width of the beam deflection becomes very large. Therefore, as described above, the influence of the aberration of the electron optics becomes large.

Figure 7:
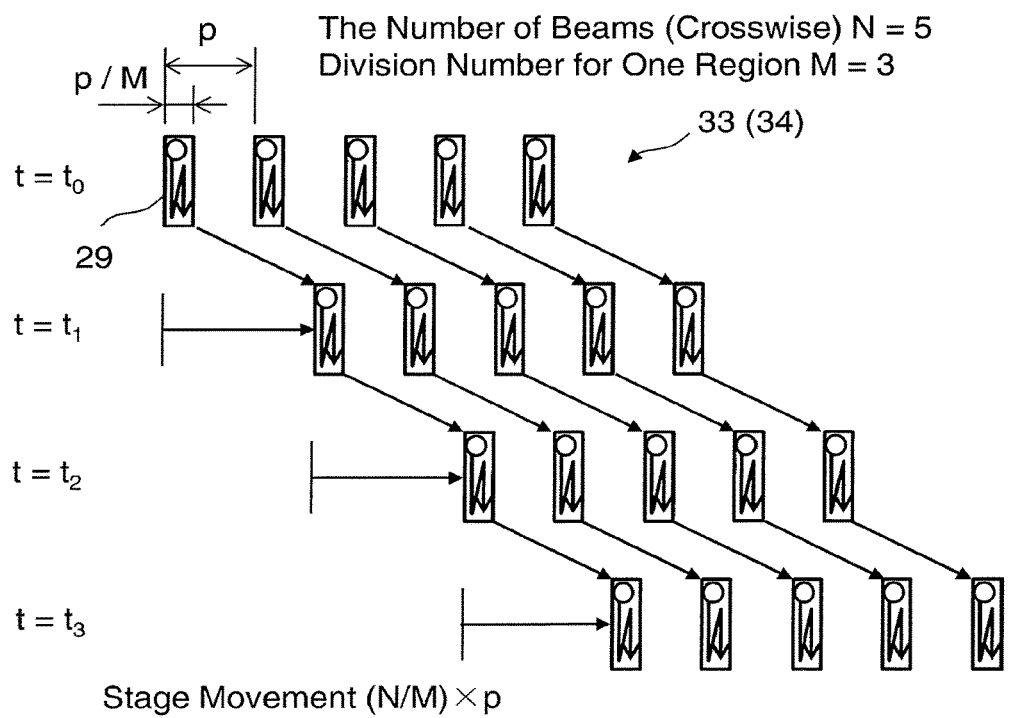
FIG. 7 is a conceptual diagram for describing an example of details of the scanning operation according to the first embodiment.

FIG. 7 is a conceptual diagram for describing an example of details of the scanning operation according to the first embodiment. In the example of FIG. 7, as the first embodiment, N multiple beams corresponding to one column in the y direction out of the N×N' multiple beams 20 are illustrated. Here, similarly to FIG. 6, N=5 multiple beams arranged in the x direction at an equal pitch p are illustrated. In first embodiment, one measurement pixel 28 out of four adjacent measurement pixels 28 is set as one of the four corners of a rectangle. From the measurement pixel 28 as a start point, a region 27 surrounded by p×p in the x and y directions is divided by a division number M. Accordingly, one grid 29 (sub region, small region) is formed by a rectangular region having a size of p/M in the x direction and p (predetermined size) in the −y direction. In the example of FIG. 7, the case where the division number M=3 is illustrated. In the comparative example of the first embodiment, a case where each beam of N=5 multiple beams arranged in the x direction at an equal pitch p scans a grid 29 (sub region) having a size p/M in the x direction and p (predetermined size) in the y direction starting from the measurement pixel 28, and then scans a next grid 29 that is N grids 29 away in the x direction.

In FIG. 7, according to the first embodiment, the XY stage 105 moves by N/M×p when the stage speed is similarly to the comparative example in FIG. 6 during the scanning of the grid 29 surrounded by (p/M)×p (period from t=t0 to t1). During the time, the main deflector 208 performs tracking deflection with N grids 29 each having a size of (p/M)×p and arranged at the pitch p in the x direction as a tracking region 33 such that the deflecting operation of the sub deflector 209 allows each beam to scan the grids 29 surrounded by (p/M)×p. At the time (t=t1) when the sub deflector 209 completes scanning of N grids 29 each having the size of (p/M)×p and arranged at the pitch p in the x direction, the main deflector 208 collectively deflect the N=5 multiple beams to positions that are separated by N grids 29 in the x direction such that scan regions do not to overlap with each other to reset tracking. In the example of FIG. 7, the main deflector 208 collectively deflects the five multiple beams to positions that are five grids 29 away. At this time, it goes without saying that the deflection position of the sub deflector 209 is reset from the last pixel 36 in the grid 29 to a first pixel 28. By repeating the above operation for the period of t=t1 to t2, the period of t=t2 to t3, and so on, even when the stage is continuously moved, scanning can be performed with the multiple beams such that the scan regions do not overlap with each other on the same stripe region 32. In the example of FIG. 7, it is necessary to deflect the multiple beams in the x direction (or −x direction) by (N−1)/M×p (=4p/M). Therefore, in first embodiment, the deflection width of beam deflection in the x direction (or −x direction) can be suppressed to (N−1)/M×p. However, without control of the relationship between the number N of beams in the x direction and the division number M, scan omission or scan duplication of a grid 29 (sub region) may be caused. According to the first embodiment, in order to apply such a scanning method, a combination of the number of beams N in the x direction and the division number M that has one as the greatest common divisor is used. With such conditions, scan omission and scan duplication can be avoided.

FIG. 8A to 8F are diagrams each illustrating an example of the relationship between the number of beams and a division number according to the first embodiment. FIG. 8A to 8F show the scanning operation in a case where the division number M is varied while using N=7 beams in the x direction. In FIG. 8A to 8F, the column is shifted every time the tracking is reset. In FIG. 8A to 8F, each of the regions 27 surrounded by p×p is illustrated with the size in the y direction reduced for convenience. In FIG. 8A, as a comparative example, a case where the division number M=1, that is, each of the regions 27 surrounded by p×p is not divided is illustrated. In FIG. 8A, when tracking is reset, the deflection width of the beam deflection increases to 6p. FIG. 8B illustrates a case where the division number M=2, that is, each of the regions 27 surrounded by p×p is divided into two. In FIG. 8B, when tracking is reset, the deflection width of the beam deflection can be reduced to 3p. FIG. 8C illustrates a case where the division number M=3, that is, each of the regions 27 surrounded by p×p is divided into three. In FIG. 8C, when the tracking is reset, the deflection width of the beam deflection can be reduced to 2p. FIG. 8D illustrates a case where the division number M=4, that is, each of the regions 27 surrounded by p×p is divided into four. In FIG. 8D, when the tracking is reset, the deflection width of the beam deflection can be reduced to (3/2)p. FIG. 8E illustrates a case where the division number M=5, that is, each of the regions 27 surrounded by p×p is divided into five. In FIG. 8E, when the tracking is reset, the deflection width of the beam deflection can be reduced to (6/5)p. FIG. 8F illustrates a case where the division number M=6, that is, each of the regions 27 surrounded by p×p is divided into six. In FIG. 8F, when the tracking is reset, the deflection width of the beam deflection can be reduced to p. By thus increasing the division number M, the deflection width of the beam deflection can be further reduced.

Here, in first embodiment, when one beam scans a sub region (grid 29) obtained by dividing a region 27 surrounded by p×p by M, and scanning is performed with the N multiple beams 20 in the x direction, N sub regions (grids 29) arranged every M are scanned at the same time. Here, a group of M×N consecutive sub regions (grids 29) is defined as one span. When the first beam in the x direction of the multiple beams 20 moves by one span, sub regions that have not been scanned remain unscanned. Here, let D be the number of sub regions that are skipped over (amount of movement) in resetting tracking. Then, while the first beam moves in the x direction by one span, tracking cycle operation is performed M×N/D times. Therefore, in order to scan all of the sub regions without overlapping or omission rather than to scan only one out of every M sub regions, the division number M and the number of tracking cycle operations have to be the same, that is, M=M×N/D has to be satisfied. Thus, D=N. Therefore, according to the first embodiment, the number D of the sub regions to be skipped over in resetting tracking has the same value as the number N of beams in the x direction. In addition, the deflection width of the beams in this case is (N−1) p/M.

When N sub regions (grids 29) each positioned in every M sub regions are scanned at the same time and the number of sub regions that are skipped over in resetting tracking is set to N, the following relationship has to be satisfied to prevent overlapping of scanning ranges in one span.
0, M, 2M, 3M, . . . , (N−1)M, NM
0, N, 2N, 3N, . . . , (M−1)N, MN It is necessary to ensure that these two sequences do not have the same value in the middle. Therefore, a combination of the number of beams N in the x direction and the division number M that has one as the greatest common divisor (relatively prime relationship between the number of beams N and the division number M) is necessary. In the examples of FIG. 8A to 8F, the two sequences have the same value in the middle when the division number M=7. Specifically, when tracking is reset, since a sub region after movement has been already scanned with an adjacent beam, scanning of the region is duplicated, which is not desirable.

Figure 8:
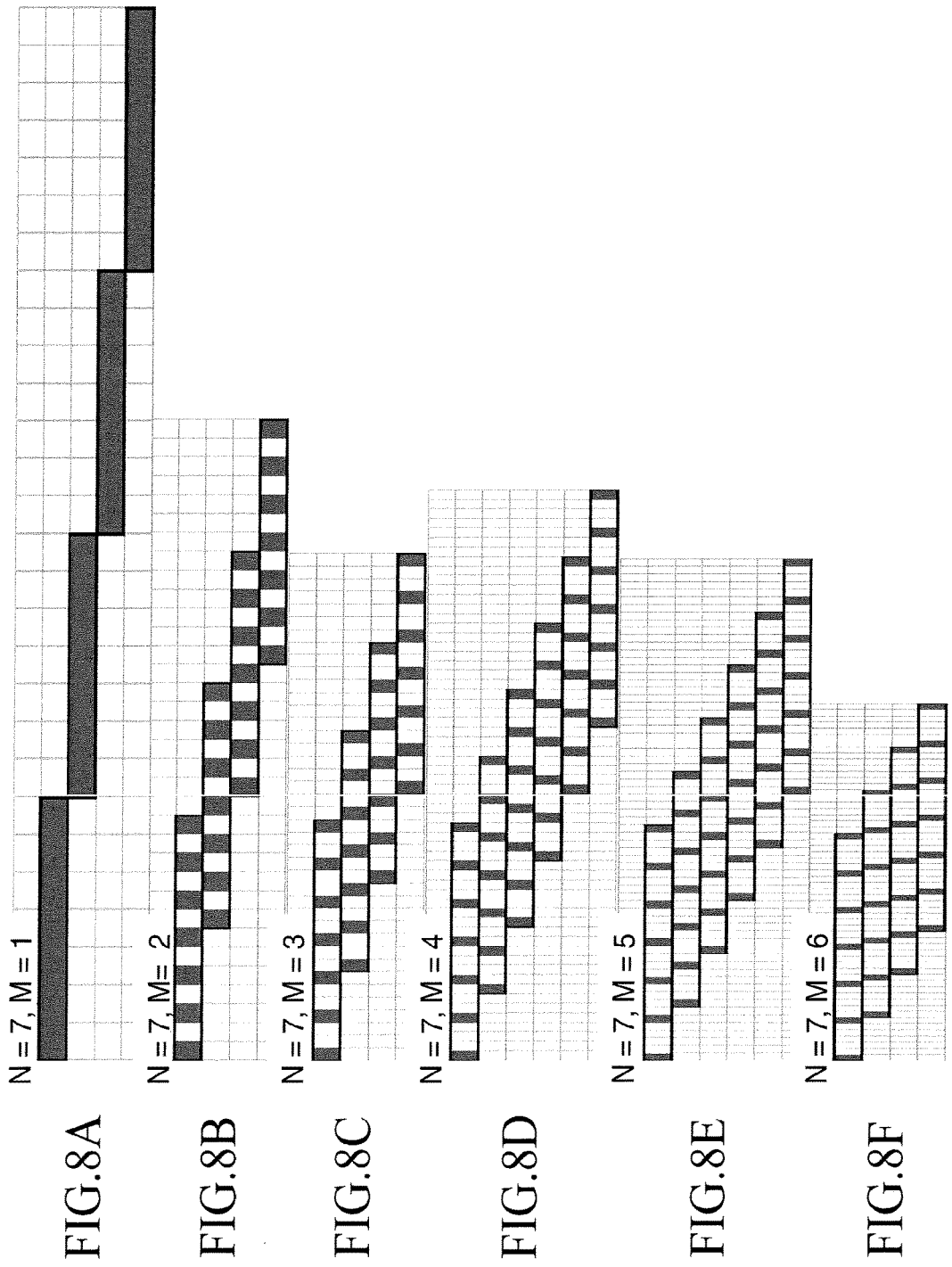
FIGS. 8A to 8F are diagrams each illustrating an example of the relationship between the number of beams and a division number according to the first embodiment.

As illustrated in the example of FIG. 8A to 8 F, it is more preferable to use a prime number as the number N of beams. By setting the number N of beams to a prime number (for example, 2, 3, 5, 7, 11, 13, 17, 23, . . . ), the degree of freedom of the division number M can be dramatically increased.

Figure 9:
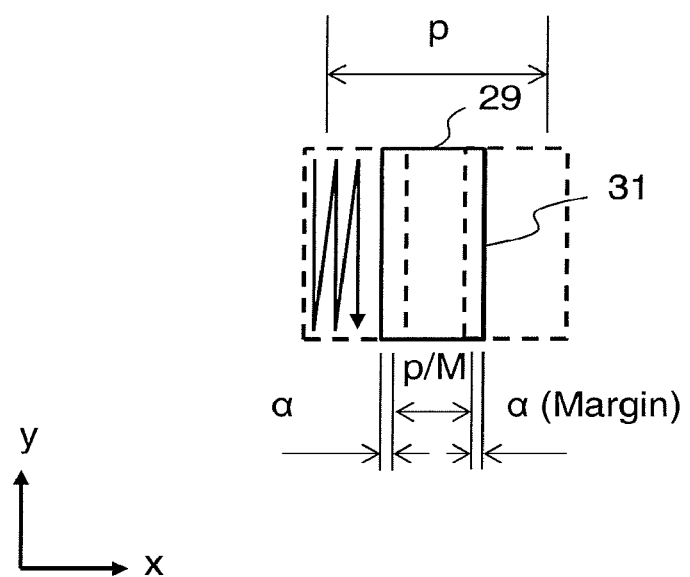
FIG. 9 is a diagram illustrating a relationship between sub regions and a scan region according to the first embodiment.

FIG. 9 illustrates a relationship between a sub regions and a scan region according to the first embodiment. A scan region 31 of each of the beams when each beam of the multiple beams 20 scans a corresponding sub region (grid 29) is preferably set to overlap with a portion of an adjacent sub region (grid 29) as illustrated in FIG. 9. Adjacent sub regions (grids 29) are scanned with different beams out of the multiple beams 20. Therefore, pitches between beams p may vary not to be equal pitches due to the influence of the aberration of the optics. Therefore, a margin width α capable of absorbing such variation is preferably provided. Therefore, the scan region 31 in actual scanning is preferably obtained by adding the margin width α to the sub region (grid 29) on at least one of its both ends in the x direction. By adding this margin, the scanning end position moves by the margin width α in the x direction. When the margin width α is provided on both sides, the scanning start position also moves in the −x direction by the margin width α. In FIG. 9, the margin width α is added in the x direction, but it is more preferable to add the margin width α in the y direction as well.

As described with reference to FIG. 8A to 8 F, the deflection width of the beams can be reduced by increasing the division number M. Therefore, from the viewpoint of reducing the deflection width of the beams, it is preferable that the division number is large. On the other hand, if the division number M is increased, the number of sub regions (grids 29) is increased, so that the number of overlapping portions is increased and wasteful image data is increased. This increases the amount of data. Therefore, from the viewpoint of reducing the amount of data, it is desirable that the division number be small. Therefore, it is more preferable to select the minimum value among the division numbers M that can provide deflection widths of the beams with which the influence of the aberration of the electron optics can be ignored.

Figure 10:
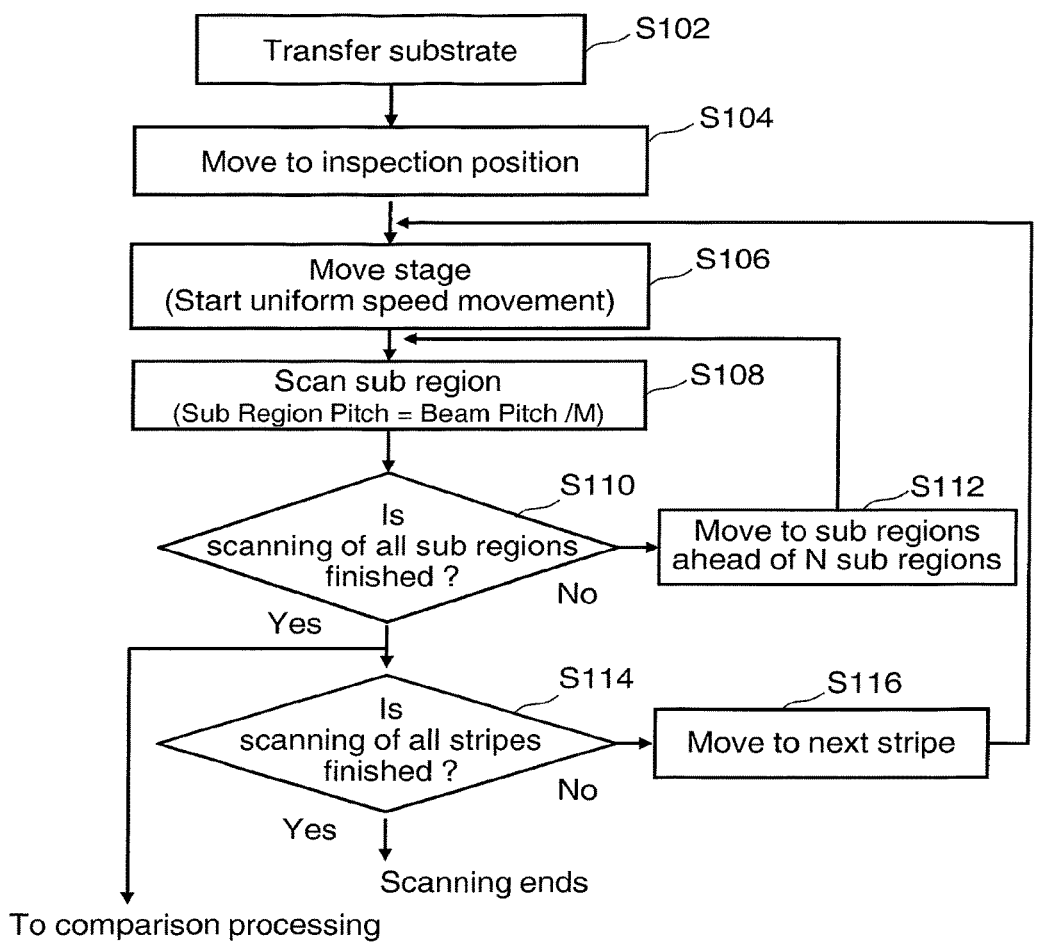
FIG. 10 is a flowchart illustrating a part of main steps of an inspection method according to the first embodiment.

FIG. 10 is a flowchart illustrating a part of main steps of the inspection method according to the first embodiment. FIG. 10 illustrates steps from the start to the end of scanning out of the main steps of the inspection method. In FIG. 10, the inspection method according to the first embodiment includes sequential steps: a substrate transfer step (S102), an inspection position moving step (S104), a stage moving step (start of uniform speed movement) (S106), a sub region scanning step (S108), a determination step (S110), a tracking reset step (S112), a determination step (S114), and a stripe movement step (S116).

In the substrate transfer step (S102), a substrate to be inspected 101 is transferred into the inspection chamber 103 by using a transport mechanism (not illustrated) and placed on the XY stage 105.

As the inspection position moving step (S104), the driving mechanism 142 moves the XY stage 105 so that the inspection position enters the irradiation-enabled position with the multiple beams 20 under the control by the stage control circuit 114. First, the XY stage 105 is moved so that the irradiation region 34 with the multiple beams 20 is positioned on the left end of the first stripe region 32 (for example, a position that is outward by the size of two irradiation regions 34).

Under the control by the stage control circuit 114, the driving mechanism 142 moves the XY stage 105 at a uniform speed, for example, at the speed V in the −x direction, as a stage moving step (start of uniform speed continuous movement) (S106). Thus, the uniform speed continuous movement is started.

As the sub region scanning step (S108), the electro-optic image acquiring mechanism 150 scans a plurality of grids 29 (sub regions, small regions) by scanning a group of N×N' grids 29 at a time. The plurality of grids 29 are obtained by dividing a stripe region 32 to be an inspection region of the substrate 101 by a size p/M (M is an integer of 2 or larger) in the x direction and a size of p (predetermined size) in the y direction. More specifically, tracking is started with N×N' multiple beams collectively deflected to a group of N×N' grids 29 on the substrate 101 arranged in N rows in the x direction and N' columns in the y direction at the pitch p, out of the plurality of grids 29. The group of N×N' grids 29 are scanned with N×N' multiple beams while tracking deflection of the multiple beams 20 is performed such that the multiple beams 20 follow the continuous movement of the XY stage 105 while the XY stage 105 moves for a distance obtained by N/M×p in the −x direction.

Figure 11:
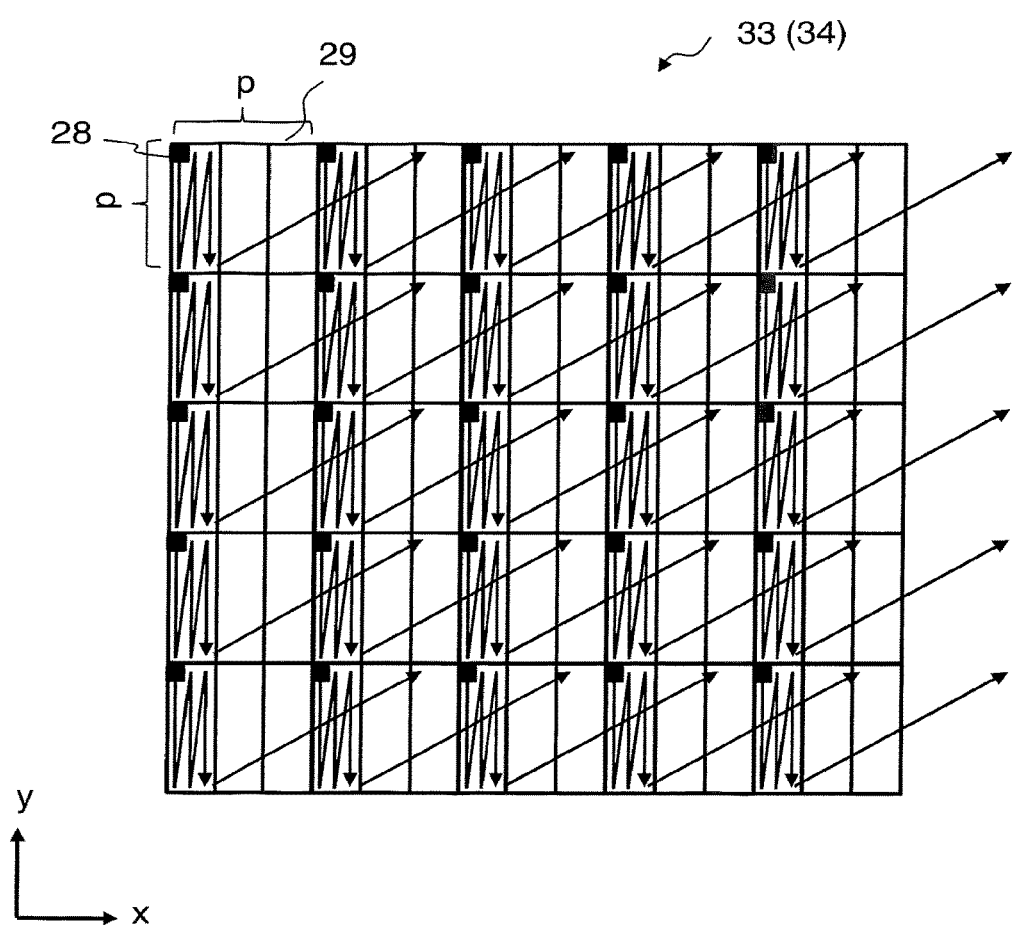
FIG. 11 is a conceptual diagram for describing another example of details of the scanning operation according to the first embodiment.

FIG. 11 is a conceptual diagram for describing another example of details of the scanning operation according to the first embodiment. The multiple beams 20 includes a plurality of electron beams arranged in N (N is an integer of 2 or more) rows in the x direction and N' (N' is an integer of 1 or more) columns in the y direction (second direction) orthogonal to the x direction at an equal pitch p (predetermined size) on the surface of the substrate 101. In the example of FIG. 11, 5×5 multiple beams arranged in the x direction and the y direction at an equal pitch p on the surface of the substrate 101 are illustrated as the N×N' multiple beams 20. It should be noted that the pitch in the y direction may be different from the pitch in the x direction. One of the four adjacent measurement pixels 28 is set as one of the four corners of a rectangle. From the measurement pixel 28 as a start point, a region 27 surrounded by p×p in the x and y directions is divided by a division number M in the x direction. Therefore, one grid 29 (sub region, small region) is constituted by a rectangular region having a size of p/M in the x direction and p in the −y direction. Therefore, in the example of FIG. 11, a case where the division number M=3 is illustrated. In the example of FIG. 11, each beam of 5×5 multiple beams scans the corresponding grid 29 (sub region), and after the scanning, scans a next grid 29 that is N (five in this case) grids away in the x direction.

First, under the control by the deflection control circuit 128, the main deflector 208 (first deflector) deflects the multiple beams 20 to the group of N×N' grids 29 arranged in N rows in the x directions and N' columns in the y direction at the pitch p out of the plurality of grids 29 obtained by dividing a region 32 (inspection region) of the substrate 101 by a size of p/M (M is an integer of 2 or larger) in the x direction and a size of p in the y direction on the surface of the substrate 101. Here, the multiple beams 20 are deflected with the group of N×N' grids 29 arranged at the pitch p in the x direction out of the plurality of grids 29 in the irradiation region 34 with the multiple beams 20 set as the tracking region 33. The main deflector 208 collectively deflects the multiple beams 20 to reference positions (for example, the center) in the tracking region 33. The main deflector 208 performs tracking deflection of the multiple beams 20 such that the multiple beams 20 follow the continuous movement of the XY stage 105.

Under the control by the deflection control circuit 128, the sub deflector 209 (second deflector) deflects the multiple beams 20 such that each of the multiple beams 20 are positioned at pixels 36 that are, for example, first in the x direction and last in the y direction of the corresponding grids 29. Actually, the multiple beams 20 are deflected such that each of the multiple beams 20 is positioned at a pixel 36 that is, for example, first in the x direction and uppermost in the y direction of the scan region 31 obtained by adding a margin to the corresponding grid 29. While the multiple beams 20 is being tracking-deflected so as to follow the continuous movement of the XY stage 105, the multiple beams 20 are collectively deflected so as to scan the N×N' grids 29 (specifically, the scan regions 31) set as the tracking region 33. In each shot, with each beam, one measurement pixel 36 corresponding to the same position in a grid 29 to be irradiated with the beam is irradiated. In the example of FIG. 11, with each beam, a measurement pixel 36 that is first from the left in the uppermost column in the grid 29 to be irradiated with the beam is irradiated as the first shot. Then, the sub deflector 209 collectively shifts the beam deflection positions for the multiple beams 20 by one measurement pixel 36 in the −y direction to irradiate measurement pixels 36 that are first from the left in the second columns from the top in the grids 29 to be irradiated with the beams as the second shot. Such scanning is repeated. After finishing irradiation of measurement pixels 36 that are the first from the left in the lowermost columns, the sub deflector 209 shifts the beam deflection positions to measurement pixels 36 that are the second measurement pixels 36 from the left in the uppermost columns while shifting all of the multiple beams 20 collectively by one measurement pixel 36 in the x direction. Such operation is repeated to sequentially irradiate all of the measurement pixels 36 in one grid 29 with one beam while the XY stage 105 continuously moves by the distance obtained by N/M×p in the −x direction. Such an operation is simultaneously performed with N×N' multiple beams 20. The multiple beams 20 formed by passing through the respective holes 22 of the shaping aperture array substrate 203 enables detection of multiple secondary electrons 300 formed of a flux of secondary electrons corresponding to a plurality of beams at once, the number of which is the same as the number of the holes 22 at most. The main deflector 208 deflects the multiple beams 20 such that the multiple beams follow the movement of the XY stage 105 (tracking operation) in order that the deflection position does not deviate due to movement of the XY stage 105 until each of the multiple beams 20 scans all of the measurement pixels 36 in the grid 29 to be irradiated with the beam.

As a detecting step, the multi-detector 222 detects secondary electrons emitted from the substrate 101 due to irradiation of the substrate 101 with the multiple beams 20. Each beam scans one corresponding grid 29. By each shot of the multiple beams 20, secondary electrons are emitted upward from the irradiated measurement pixels 36. In this manner, the multi-detector 222 detects the secondary electrons emitted from the substrate 101 due to irradiation of the substrate 101 with the multiple beams 20. The multi-detector 222 detects multiple secondary electrons 300 emitted upward from the respective measurement pixels 36 for each of the measurement pixels 36.

As the determination step (S110), the control computer 110 determines whether all of the grids 29 in the target stripes 32 is finished when all of the measurement pixels 36 in the grids 29 (more specifically, the scan regions 31) to be irradiated with the respective beams 20 are scanned. When scanning of all of the grids 29 in the target stripes 32 is finished, the process proceeds to the determination step (S114). When scanning of all of the grids 29 in the target stripes 32 is not finished, the process proceeds to the tracking reset step (S112).

As the tracking reset step (S112), after scanning all of the measurement pixels 36 in the grids 29 (more specifically, the scan regions 31) to be irradiated with the respective beams 20 by the deflection operation of the sub deflector 209, the main deflector 208 re-deflect the multiple beams 20 collectively to a new group (next group) of N×N' grids 29 (more specifically, the scan regions 31) arrayed at the pitch p in the x direction, that is N grids 29 away from the N×N' grids 29 in the x direction by the time when the movement of the XY stage 105 in the −x direction by a distance obtained by N/M×p is completed, thereby resetting tracking.

In the example of FIG. 11, a new group of N×N' grids 29 (more specifically, the scan regions 31) that are away by 5 grids 29 in the x direction is reset to a new tracking region 33. The main deflector 208 performs tracking deflection of the multiple beams 20 such that the multiple beams 20 follow the continuous movement of the XY stage 105. Also, at the time of the tracking reset, the sub deflector 209 (the second deflector) deflects the multiple beams 20 collectively such that the respect beams of the multiple beams 20 are positioned at pixels 36 that are firs in the x direction and last in the y direction of the corresponding grids 29 (specifically, the scan regions 31).

Then, the tracking cycle from the start of tracking to the tracking reset and the scan during tracking are repeated. In other words, as described above, while the multiple beams 20 are tracking-deflected such that the multiple beams 20 follow the continuous movement of the XY stage 105, a group of N×N' grids 29 (specifically, scan regions 31) set as a tracking region 33 is scanned. By repeating the operation, all of the pixels 36 in the stripe region 32 can be scanned.

In the above description, each shot is described as the first shot, the second shot, . . . , but the multiple beams 20 may perform raster scanning operation, in which the deflection position is moved while continuing the irradiation without turning ON/OFF the beam for each of the pixels 36. Further, the present invention is not limited to the case where respective pixels in each row arranged in the y direction are scanned in the same direction. The pixel row of the first row in the x direction may be scanned in the −y direction and then the pixel row of the second row may be scanned in the y direction (opposite direction).

Figure 12:
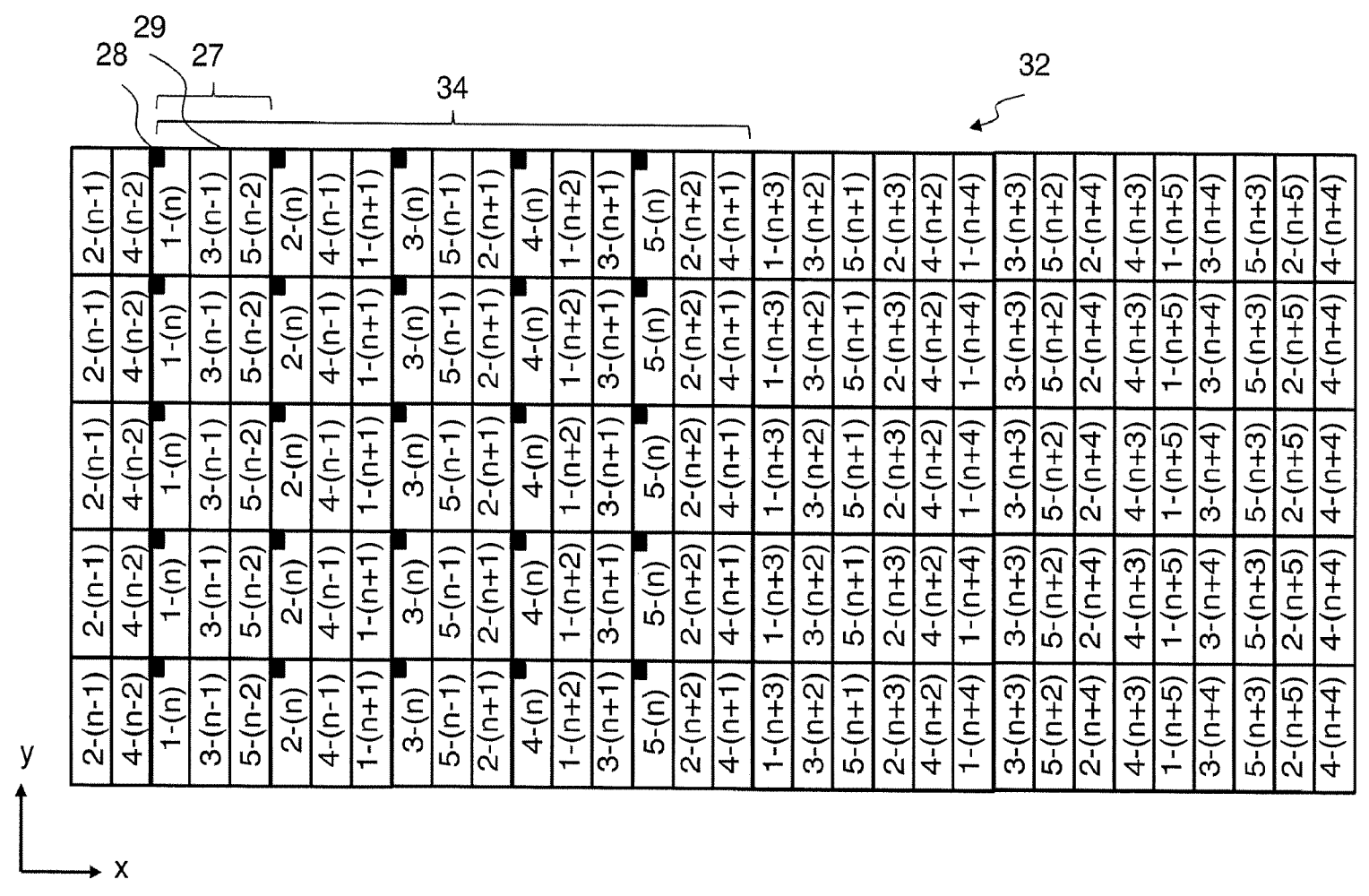

FIG. 12 is a conceptual diagram for describing an example of the relationship between the sub regions and the corresponding beams in the scanning operation according to the first embodiment. In the example of FIG. 12, 5×5 multiple beams 20 arranged at an equal pitch p in the x and y directions are used. In addition, in the illustrated example, the division number M=3. In the example of FIG. 12, the width (size in the y direction) of the stripe region 32 is divided according to the size of the irradiation region 34. Therefore, the stripe region 32 is divided into a plurality of grids 29 having a size of p/M (=p/3) in the x direction and a size pin they direction. In the example of FIG. 12, the plurality of grids 29 are obtained by dividing the stripe region 32 into five columns in the y direction, and a plurality of grids 29 in one column arranged in the x direction is scanned by N (=5) multiple beams 20. As illustrated in FIG. 12, grids (29) scanned in n th tracking cycle with the five beams (1 to 5) for each column are respectively labeled 1-($n$), 2-($n$), 3-($n$), 4-($n$), and 5-($n$). When the n th tracking is reset, the main deflector 208 re-deflects the beams to grids 29 that are ahead of N (=5) grids. Thus, the grids 29 ahead of 5 grids 29 will be scanned in the (n+1) th tracking cycle. The grids 29 scanned in the (n+1) th tracking cycle are respectively labeled 1-($n$+1), 2-($n$+1), 3-($n$+1), 4-($n$+1), and 5-($n$+1). By repeating the similar operation, all of the grids 29 can be scanned.

For example, in the p×p region 27 including a grid 29 that is uppermost and scanned with the first beam in n th tracking cycle, two grids 29 are remained out of the three grids obtained by dividing the region 27 into three. The grid adjacent to the grid 29 labeled 1-($n$) in the x direction (right side) will be scanned in the (n−1) th tracking cycle with the third beam. Furthermore, the grid adjacent to the adjacent grid in the x direction (right side) will be scanned in the (n−2) th tracking cycle with the fifth beam. Through these three tracking cycles, scanning within the p×p region 27 is completed. It is the same in each column in the y direction.

For example, in the p×p region 27 including a grid 29 that is uppermost and scanned with the second beam in n th tracking cycle, two grids 29 are remained out of the three grids obtained by dividing the region 27 into three. The grid adjacent to the grid 29 labeled 2-($n$) in the x direction (right side) will be scanned in the (n−1) th tracking cycle with the fourth beam. Furthermore, the grid adjacent to the adjacent grid in the x direction (right side) will be scanned in the (n+1) th tracking cycle with the first beam. Through these three tracking cycles, scanning within the p×p region 27 is completed. It is the same in each column in the y direction.

For example, in the p×p region 27 including a grid 29 that is uppermost and scanned with the third beam in n th tracking cycle, two grids 29 are remained out of the three grids obtained by dividing the region 27 into three. The grid adjacent to the grid 29 labeled 3-($n$) in the x direction (right side) will be scanned in the (n−1) th tracking cycle with the fifth beam. Furthermore, the grid adjacent to the adjacent grid in the x direction (right side) will be scanned in the (n+1) th tracking cycle with the second beam. Through these three tracking cycles, scanning within the p×p region 27 is completed. It is the same in each column in the y direction.

For example, in the p×p region 27 including a grid 29 that is uppermost and scanned with the fourth beam in n th tracking cycle, two grids 29 are remained out of the three grids obtained by dividing the region 27 into three. The grid adjacent to the grid 29 labeled 4-($n$) in the x direction (right side) will be scanned in the (n+2) th tracking cycle with the first beam. Furthermore, the grid adjacent to the adjacent grid in the x direction (right side) will be scanned in the (n+1) th tracking cycle with the third beam. Through these three tracking cycles, scanning within the p×p region 27 is completed. It is the same in each column in the y direction.

For example, in the p×p region 27 including a grid 29 that is uppermost and scanned with the fifth beam in n th tracking cycle, two grids 29 are remained out of the three grids obtained by dividing the region 27 into three. The grid adjacent to the grid 29 labeled 5-(*n*) in the x direction (right side) will be scanned in the (n+2) th tracking cycle with the second beam. Furthermore, the grid adjacent to the adjacent grid in the x direction (right side) will be scanned in the (n+1) th tracking cycle with the fourth beam. Through these three tracking cycles, scanning within the p×p region 27 is completed. It is the same in each column in the y direction.

Therefore, when the stripe region 32 is scanned by using the division number M=3 and N=5 multiple beams, scanning operation is started at a position outside from the end on the scanning start side of the stripe regions 32 where a grid 29 that is closer to the end on the scanning start side by at least two tracking cycles can be scanned with the fifth beam.

By scanning using the multiple beams 20 as described above, scanning operation (measurement) can be performed at a higher speed than scanning with a single beam.

In the determination step (S114), the control computer 110 determines whether scanning of all of the stripes 32 has finished. When all of the stripes 32 have been scanned, the electro-optical image acquisition process ends. When all of the stripes 32 have been scanned, the process proceeds to the stripe moving step (S116).

In the stripe moving step (S116), under the control of the stage control circuit 114, the driving mechanism 142 moves the XY stage 105 such that the irradiation region 34 of the multiple beams 20 is positioned on the left side of the next stripe region 32 (for example, outer side by one irradiation region 34). The above steps are then repeated.

Figure 13:
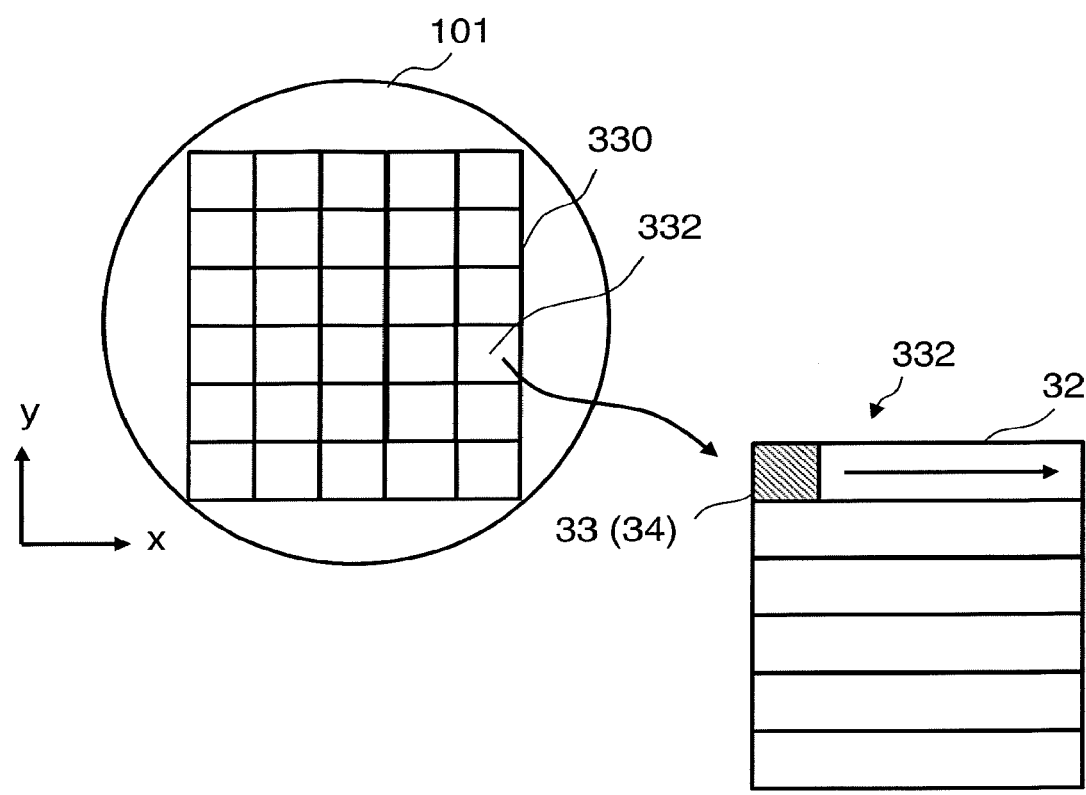
FIG. 13 is a conceptual diagram for describing another example of the scanning operation according to the first embodiment.

FIG. 13 is a conceptual diagram for describing another example of the scanning operation according to the first embodiment. As illustrated in FIG. 13, a plurality of chips 332 (dies) having a predetermined width are formed in the inspection region 330 of the substrate 101 in, for example, an array in the x and y directions. In this case, it is preferable to adapt to a semiconductor substrate (for example, a wafer) as a substrate 101 to be inspected. Each of the chips 332 is formed on the substrate 101 in a size of 30 mm×25 mm, for example. Pattern inspection will be performed for each of the chips 332. The region of each chip 332 is virtually divided into a plurality of stripe regions 32 to have a width that is the same as that of the irradiation region 34 which can be irradiated by irradiation with all of the multiple beams 20 once. The scanning operation of each stripe region 32 may be the same as that described above. As described above, according to the first embodiment, by continuously moving the XY stage 105 in the −x direction, the respective stripe regions 32 are scanned with the multiple beams 20 while the irradiation region 34 is relatively moved in the x direction to scan. When scanning of all of the stripe regions 32 is finished, the stage position is moved in the −y direction and the stripe regions 32 of the next column that have the same size in the y direction are similarly scanned with the multiple beams 20. When this operation is repeated and the scanning of the regions of one chip 332 is completed, the XY stage 105 is moved and the scanning operation is similarly performed on the stripe region 32 that is uppermost of the next chip 332. By repeating such operations, scanning is performed for all of the chips 332.

As described above, the electro-optic image acquiring mechanism 150 scans the substrate 101 to be inspected on which the figure pattern is formed by using the multiple beams 20 of a plurality of electron beams while continuously moving the XY stage 105, and detects multiple secondary electrons 300 emitted from the substrate to be inspected 101 due to the irradiation with the multiple beams 20. The way of scanning and the way of detecting the multiple secondary electrons 300 are as described above. Detection data of secondary electrons from each measurement pixel 36 detected by the multi-detector 222 is output to the detection circuit 106 in the order of measurement. In the detection circuit 106, analog detection data is converted into digital data by an A/D converter (not illustrated) and stored in the stripe pattern memory 123. When the detection data of one stripe region 32 (or one chip 332) is stored, the data is transferred to the comparator circuit 108 as stripe pattern data (or chip pattern data), together with the information indicating each position from the position circuit 107.

Meanwhile, a reference image is created concurrently with, or before or after the scanning step with the multiple beams and the secondary electron detection step.

As a reference image creating step, the reference image generating unit such as the pattern generation circuit 111 and the reference image generation circuit 112 generates, when the substrate 101 is a semiconductor substrate, a reference image of a region corresponding to a measurement image (electro-optic image) of a frame region having a size equal to or less than a grid 29 composed of a plurality of pixels 36 (to be described later) is created based on exposure image data that defines an exposure image on the substrate when the mask pattern of the exposure mask is exposure-transferred to the semiconductor substrate. Instead of the exposure image data, pattern data (design data) used as a basis for forming an exposure mask for exposure-transferring a plurality of figure patterns to the substrate 101 may be used. In a case where the substrate 101 is an exposure mask, the reference image generating unit such as the pattern generation circuit 111 and the reference image generation circuit 112 generates a reference image of a region corresponding to the measurement image (electro-optic image) of a frame region constituted by the plurality of pixels 36 based on the pattern data (design data) to be a basis for forming a plurality of figure patterns on the substrate 101.

Specifically, the reference image generating unit operates as follows. First, the pattern generation circuit 111 reads pattern data (or exposure image data) from the storage device 109 via the control computer 110, converts a figure pattern of each frame region defined in the read pattern data (or exposure image data) to a binary or multi-valued image data piece, and transmits this image data piece to the reference image generation circuit 112.

Here, the figure defined in the pattern data (or the exposure image data) is, for example, based on a rectangle or a triangle, and figure data defining a shape, a size, a position, and the like of each pattern figure using information including, for example, coordinates (x, y) at reference positions of the figure, lengths of sides, a figure code that is an identifier to identify a figure type, such as rectangle or triangle is stored.

When pattern data (or exposure image data) to be the figure data is input to the pattern generation circuit 111, the pattern generation circuit 111 develops the pattern data to data pieces for respective figures and interprets figure codes, figure sizes, and the like that indicate the figure shapes of the figure data. The pattern generation circuit 111 then develops the binary or multi-valued design image data as a pattern arranged in squares having a grid of a predetermined quantized grid size as a unit and outputs the pattern. In other words, the pattern generation circuit 111 reads the design data, calculates the occupation rate occupied by the figure for each of squares obtained by virtually dividing the inspection region into squares having a predetermined size as a unit, and outputs n-bit occupation radio data. For example, it is preferable to set one square as one pixel. Also, assuming that one pixel has a resolution of 1/28 (=1/256), small regions of 1/256 corresponding to the region of the figure arranged in the pixel are allocated to calculate the occupation rate in the pixel. Then, the pattern generation circuit 111 outputs 8-bit occupancy rate data to the reference image generation circuit 112. Such a square may have the same size as that of the measurement pixels 36.

Next, the reference image generation circuit 112 performs an appropriate filtering process on the design image data, which is image data of the transmitted figure. Since measurement data as an optical image obtained from the detection circuit 106 is in a state where a filter acts by the electron optics, in other words, in an analog state where data continuously varies, design image data that is image data having image intensity (gray value) as a digital value can be adjusted to match measurement data by performing filter processing on the design image data on design side. Thus, design images (reference images) to be compared with measurement images (optical images) of the frame region are formed. The pieces of image data of the formed reference images are respectively output to the comparator circuit 108, and the reference images output to the comparator circuit 108 are respectively stored in the memory.

Figure 14:
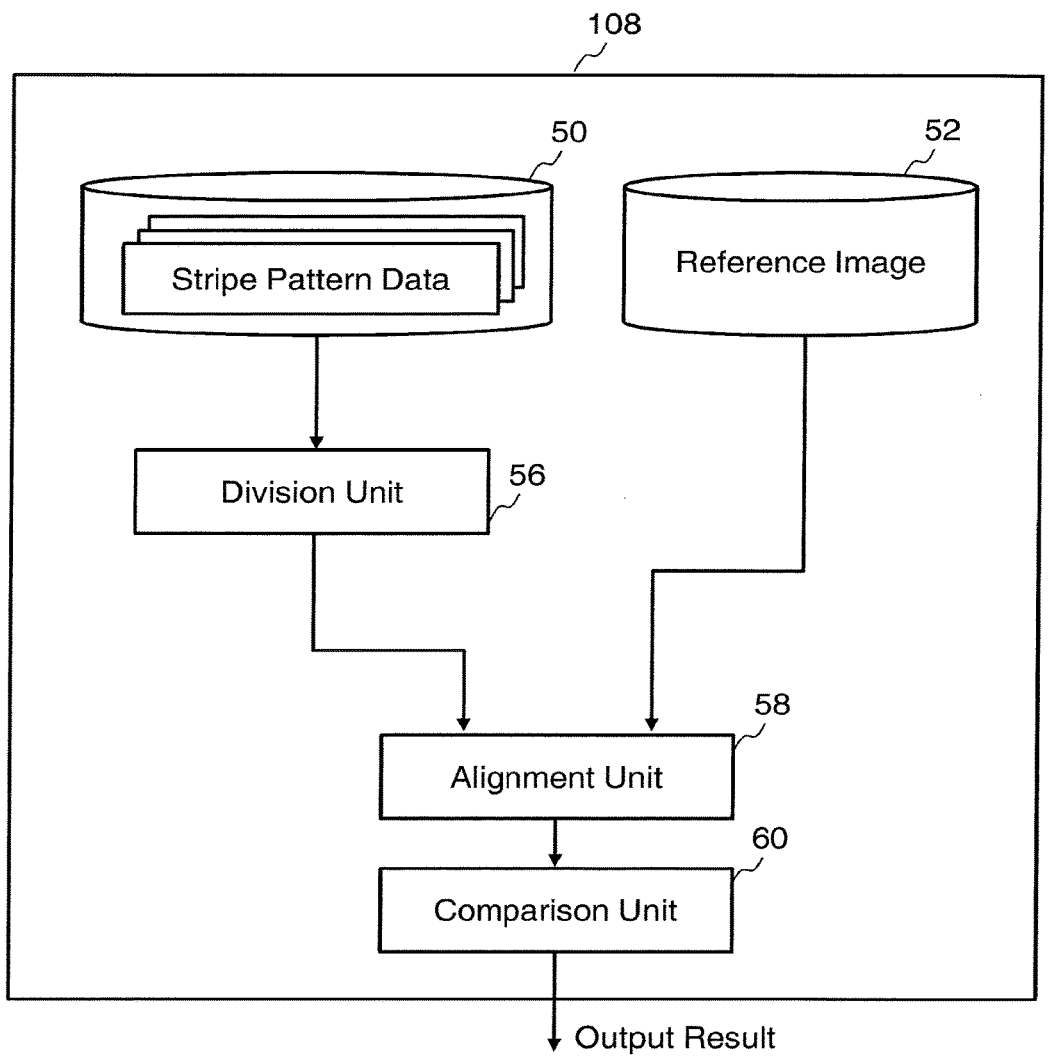
FIG. 14 is a diagram illustrating the internal configuration of a comparator circuit according to the first embodiment.

FIG. 14 is a diagram illustrating the internal configuration of the comparator circuit according to the first embodiment. In FIG. 14, in the comparator circuit 108, storage devices 50 and 52 such as a magnetic disk drive, a division unit 56, a alignment unit 58, and a comparator unit 60 are disposed. Each of the "units" such as the division unit 56, the alignment unit 58, and the comparator unit 60 includes processing circuitry, and the processing circuitry includes an electric circuit, a computer, a processor, a circuit board, a quantum circuit, a semiconductor device, and the like. In addition, the "units" may use common processing circuitry (the same processing circuitry). Alternatively, the "units" may use different pieces of processing circuitry (separate pieces of processing circuitry). The necessary input data or calculated results in the division unit 56, the alignment unit 58, and the comparator unit 60 are stored in a memory (not illustrated) each time.

The transferred stripe pattern data (or chip pattern data) is temporarily stored in the storage device 50 together with information indicating each position from the position circuit 107. Similarly, the reference image data is temporarily stored in the storage device 52 together with information indicating each design position.

Next, the division unit 56 divides the stripe pattern data (or chip pattern data) for each frame region (unit inspection region), and generates a plurality of frame images (inspection images).

Figure 15:
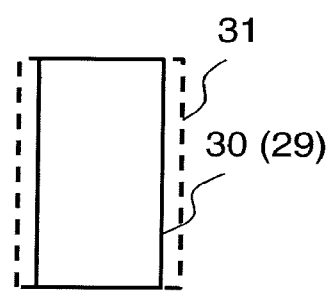
FIG. 15 is a diagram illustrating an example of the relationship between a grid and a frame region according to the first embodiment.

FIG. 15 is a diagram illustrating an example of the relationship between the grid and the frame region according to the first embodiment. As described above, each of the grids 29 is scanned with one beam. As described above, each grid 29 is scanned for each of the scan regions 31, which is larger than the grid 29 as described above, so as not to cause a joint error with a grid 29 scanned with another beam. Since there is a possibility that the characteristic of the obtained secondary electron image may vary depending on beams, it is preferable to use an image obtained by one beam for an image of one unit inspection region. Therefore, according to the first embodiment, a plurality of frame images are created by dividing the measured stripe pattern data (or chip pattern data) for each frame region 35, which is a unit inspection region. Similarly, a reference image is created for each frame region 35. In that case, the frame region 35 is set as a range to be scanned with one beam. Therefore, the frame region 35 is set to be equal to or smaller than the size of the grids 29. For example, the frame region 35 may preferably be set to a size obtained by dividing each of the grids 29 by a natural number. Thus, the division unit 56 divides a detected secondary electron image into inspection images having a size equal to or smaller than the size of the scan regions 31.

Next, the alignment unit 58 aligns the frame images (measurement images) with the reference images in sub-pixel units smaller than the pixels 36. For example, the positioning may be performed by a least square method.

The comparator unit 60 then compares each of the frame images (inspection images) with the corresponding reference image respectively. For example, the comparator unit 60 compares the frame images and the reference images for each of the pixels 36. The comparator unit 60 compares them for each of the pixels 36 according to a predetermined determination condition, and determines whether any defect such as a shape defect is present. For example, if the difference between gradation values of the respective pixels 36 is larger than a determination threshold value Th, the comparator unit 60 determines a defect is present. Alternatively, the inspection accuracy may be lowered from that for the shape defect inspection to inspect whether disconnection or short circuit of the pattern is present. For example, a pair of edges of a pattern may be detected to measure a distance between the edges in a pair. Thus, it is possible to measure the width size of a line pattern and a distance of a space portion between line patterns. Similarly, the comparator unit 60 may determine that a defect is present when difference from the distance obtained from the reference image is larger than the determination threshold value Th. It is possible to inspect whether disconnection and/or short circuit of a pattern is present by measuring distances between edges in pairs at a plurality of positions in the line direction. The comparator unit 60 then outputs the comparison result. The comparison result may be output from the storage device 109, the monitor 117, the memory 118, or the printer 119.

As described above, according to the first embodiment, in the pattern inspection performed using the multiple beams 20 arranged in the movement direction of the XY stage 105 while the XY stage 105 is moved continuously, the deflection width of the beam deflection can be reduced. Therefore, the influence of the aberration of the optics can be suppressed. Further, throughput can be improved in the pattern inspection by using the multiple beams 20.

In the above description, a series of "circuits" includes processing circuitry, and the processing circuitry includes an electric circuit, a computer, a processor, a circuit board, a quantum circuit, a semiconductor device, and the like. In addition, the "circuits" may use common processing circuitry (the same processing circuit). Alternatively, the "circuits" may use different pieces of processing circuitry (separate pieces of processing circuitry). A program to be executed by a processor or the like may be stored in a recording medium such as a magnetic disk drive, a magnetic tape device, an FD, or a ROM (read only memory).

The embodiment has been described with reference to specific examples. However, the present invention is not limited to these specific examples. In the above examples, a case where the XY stage 105 is moved continuously at a uniform speed is illustrated, but the present invention is not limited to this case. Continuous uniform speed movement is desirable from the viewpoint of ease of control, but it may be continuous movement accompanying acceleration or deceleration. In addition, regarding the relation between the number of beams N in the continuous movement direction (the −x direction in the embodiment) of the XY stage 105 during scanning and the division number M, either one may be larger as long as the minimum common divisor between the values is 1.

In the above example, a case of using multi-stage deflectors, which is two-stage deflectors including the main and sub deflectors (the main deflector 208 and the sub deflector 209) for the tracking deflection and the deflection for scanning in the grids 29 is illustrated, but the invention is not limited to this case. It is also preferable to perform deflection control of both the tracking deflection and the deflection for scanning in the grids 29 using the same deflector. This can be performed by applying a voltage obtained by adding the deflection voltage for tracking deflection and the deflection voltage for deflection for scanning in the grids 29 to each electrode constituting the deflector. Such control of the deflection voltage may be performed by the deflection control circuit 128.

In particular, when the same deflector performs deflection control of both the tracking deflection and the deflection for scanning in the grids 29, it may be preferable to set N and M such that the deflection amplitude (N−1) p/M of the beams in the x direction and the deflection amplitude p of the beams in the y direction are the same. By adjusting the deflection widths in two directions, it is easy to control the settling time of an amplifier or the like (not illustrated).

The order of irradiation with beams in scanning in a grid 29 (scan region 31) may be arbitrary. However, since the sub deflector 209 deflects all of the multiple beams 20 collectively, the order of irradiation becomes the same for the respective grids 29.

Further, in the above-described example, a case where the beams are arranged in an orthogonal grid is illustrated, but the present invention is not limited thereto. For example, a diagonal grid may be used. Alternatively, beam columns arranged in the y direction each including a row of beams arranged in the x direction may be arranged to be slightly shifted in the x direction. For example, the leading ends of the rows of beams arranged in the x direction may be arranged irregularly.

The shape of the grids 29 (sub regions, small regions) described above is not limited to the rectangular shape. The grids 29 may have any shape as long as they are arranged at a pitch of p/M in the x direction and at an equal pitch in the y direction. The shape of the grids 29 (sub regions, small regions) may be, for example, a parallelogram. In this case, it is preferable to make the scan regions 31 have a parallelogram shape according to the shape of the grids 29. In a case of parallelogram, scanning beams obliquely can easily avoid scanning in parallel with the circuit pattern since the circuit pattern has lines that are mostly parallel with and/or orthogonal to the x direction. Thus, it is possible to avoid the influence of charging.

In addition, the arrangement pitches in the x direction and the y direction of the multiple beams 20 may be different. For example, they may be arranged at an equal pitch p in the x direction and arranged at an equal pitch p' in the y direction.

In addition, descriptions of parts and the like which are not directly required for the description of the present invention such as an apparatus configuration and a control method are not described, but a necessary apparatus configuration and a control method can be appropriately selected and used.

In addition, all electron beam inspection apparatuses and electron beam inspection methods that include the components of the present invention and that can be obtained through appropriate design change by those skilled in the art are encompassed in the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A charged particle beam inspection apparatus comprising:
   a movable stage on which an inspection target substrate is placed;
   a stage control circuit configured to continuously move the stage in a direction opposite to a first direction;
   a first deflector configured to deflect multiple beams composed of a plurality of charged particle beams arrayed in N (N is an integer of 2 or larger) rows at an equal pitch p in the first direction and N' (N' is an integer of 1 or larger) columns in a second direction that is orthogonal to the first direction on the substrate collectively to a group of N×N' small regions arrayed in N rows at the pitch p in the first direction and N' columns in the second direction among a plurality of small regions obtained by dividing an inspection region of the substrate by a size p/M (M is an integer of 2 or larger) in the first direction and a predetermined size in the second direction, perform tracking deflection of the multiple beams such that the multiple beams follow movement of the stage while the stage continuously moves a distance obtained by N/M×p in the direction opposite to the first direction, and re-deflect the multiple beams collectively to a next group of N×N' small regions arrayed at the pitch p in the first direction, the next group being away from the group of N×N' small regions by N small regions in the first direction by the stage completes the movement of the distance obtained by N/M×p in the opposite direction of the first direction so as to reset the tracking deflection;
   a second deflector configured to deflect the multiple beams collectively such that the group of N×N' small regions concerned are scanned while the tracking deflection of the multiple beams are performed to follow the continuous movement of the stage; and
   a detector configured to detect secondary electrons emitted from the substrate due to irradiating the substrate with the multiple beams,
   wherein a combination of the numbers N and M that has one as the greatest common divisor is used.

2. The apparatus according to claim 1, wherein a scan region of each beam, when each beam of the multiple beams scans a corresponding small region of the N×N' small regions, is set to overlap with a portion of an adjacent small region of the corresponding small region.

3. The apparatus according to claim 2 further comprising:
   division processing circuitry configured to divide a detected secondary electron image into inspection images having a size equal to or smaller than a size of the scan region; and
   comparison processing circuitry configured to compare each of the inspection images with a corresponding reference image respectively.

4. The apparatus according to claim 1, wherein a prime number is used as the value of N.

5. The apparatus according to claim 1, wherein a size of each of the plurality of small regions in the second direction is larger than that in the first direction.

6. The apparatus according to claim 5, wherein a size of each of the plurality of small regions in the second direction is identical to the pitch p.

7. The apparatus according to claim 1, wherein a distance between a small region of the plurality of small regions scanned by one beam of the multiple beams at n th time and a small region of the plurality of small regions scanned at (n+1) th time by the beam is larger than the pitch p between beams of the multiple beams.

8. The apparatus according to claim 1, wherein the second deflector deflects the multiple beams collectively from small regions out of the plurality of small regions that are scanned at n th time by the multiple beams to small regions out of the plurality of small regions that are scanned at (n+1) th time by the multiple beams such that a beam having an adjacent beam in the first direction out of the multiple beams skips over a small region out of the plurality of small regions that is scanned at n th time by the adjacent beam in the first direction.

9. A charged particle beam inspection method comprising:
deflecting multiple beams composed of a plurality of charged particle beams arrayed in N (N is an integer of 2 or larger) rows at an equal pitch p in a first direction and N' (N' is an integer of 1 or larger) columns in a second direction that is orthogonal to the first direction on an inspection target substrate collectively to a group of N×N' small regions arrayed in N rows at the pitch p in the first direction and N' columns in the second direction among a plurality of small regions obtained by dividing an inspection region of the substrate by a size p/M (M is an integer of 2 or larger) in the first direction and a predetermined size in the second direction, and scanning the N×N' small regions while performing tracking deflection of the multiple beams such that the multiple beams follow movement of a stage on which the inspection target substrate is placed while the stage continuously moves a distance obtained by N/M×p in a direction opposite to the first direction;

detecting secondary electrons emitted from the substrate due to irradiating the substrate with the multiple beams; and performing tracking reset by re-deflecting the multiple beams collectively to a next group of N×N' small regions arrayed at the pitch p in the first direction, the next group being away from the group of N×N' small regions by N small regions by the stage completes the movement of the distance obtained by N/M×p in the opposite direction of the first direction, wherein the scanning, the detecting, and the performing tracking reset are repeated while the stage continuously moves in the direction opposite to the first direction using a combination of the numbers N and M that has one as the greatest common divisor.

10. The method according to claim 9, wherein a prime number is used as the value of N.

* * * * *